United States Patent
Morrow

(10) Patent No.: US 6,743,018 B1
(45) Date of Patent: Jun. 1, 2004

(54) DENTAL RESTORATION APPARATUS

(75) Inventor: Len W. Morrow, Lexington, KY (US)

(73) Assignee: Morrow Intellectual Properties, LLC, Lexington, KY (US)

( * ) Notice: Subject to any disclaimer, the term of this patent is extended or adjusted under 35 U.S.C. 154(b) by 112 days.

(21) Appl. No.: 09/950,336

(22) Filed: Sep. 11, 2001

Related U.S. Application Data

(63) Continuation-in-part of application No. 08/985,675, filed on Dec. 5, 1997, now abandoned, and a continuation of application No. 08/986,177, filed on Dec. 5, 1997, now abandoned.
(60) Provisional application No. 60/032,827, filed on Dec. 12, 1996.

(51) Int. Cl.$^7$ .................................................. A61C 8/00
(52) U.S. Cl. .......................... 433/173; 433/172; 411/55; 411/61; 411/71
(58) Field of Search ................................ 433/173, 174, 433/175, 176, 172, 169; 411/55, 60, 60.2, 61, 71, 74, 204, 248, 354

(56) References Cited

U.S. PATENT DOCUMENTS

| | | | | |
|---|---|---|---|---|
| 4,668,191 A | * | 5/1987 | Plischka | 433/174 |
| 4,960,381 A | | 10/1990 | Niznick | 433/174 |
| 4,988,299 A | * | 1/1991 | Branemark | 433/174 |
| 5,006,068 A | | 4/1991 | Lee et al. | 433/169 |
| 5,049,072 A | | 9/1991 | Lueschen | 433/173 |
| 5,049,073 A | * | 9/1991 | Lauks | 433/173 |
| 5,061,181 A | | 10/1991 | Niznick | 433/174 |
| 5,078,607 A | | 1/1992 | Niznick | 433/174 |
| 5,098,294 A | * | 3/1992 | Lee et al. | 433/173 |
| 5,213,500 A | | 5/1993 | Salazar et al. | 433/169 |
| 5,284,408 A | * | 2/1994 | Duran et al. | 411/55 |
| 5,314,278 A | * | 5/1994 | Weber | 411/61 |
| 5,513,989 A | * | 5/1996 | Crisio | 433/176 |
| 5,549,475 A | * | 8/1996 | Duerr et al. | 433/173 |
| 5,702,214 A | * | 12/1997 | Duran | 411/55 |
| 5,733,122 A | | 3/1998 | Gordon | 433/172 |
| 5,759,034 A | * | 6/1998 | Daftary | 433/172 |
| 5,762,500 A | | 6/1998 | Lazarof | 433/173 |

\* cited by examiner

Primary Examiner—John J. Wilson
(74) Attorney, Agent, or Firm—Stoll Keenon & Park, LLP

(57) ABSTRACT

The present invention is directed to developments in the fields of dentistry and dental surgery, and particularly to an improvement in dental restoration apparatus. Typically, apparatus of this type includes an implant adapted to be implanted in an anchor site fashioned within the bone of the jaw of the patient. In addition, the apparatus includes an abutment ultimately providing support for a tooth restoration. Finally, the apparatus includes a fastener assembly for engaging both the implant and abutment in their mounted orientation, and securing the two structures together in a manner to positively resist relative movement both axially and rotationally.

49 Claims, 14 Drawing Sheets

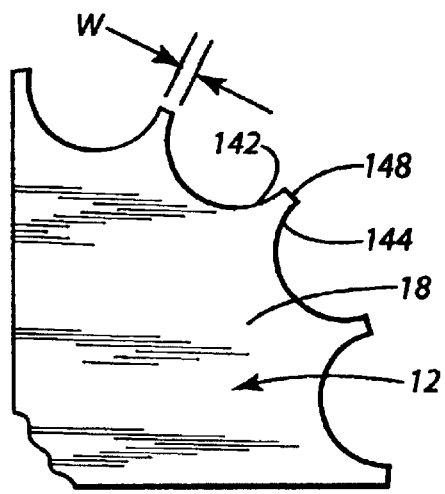
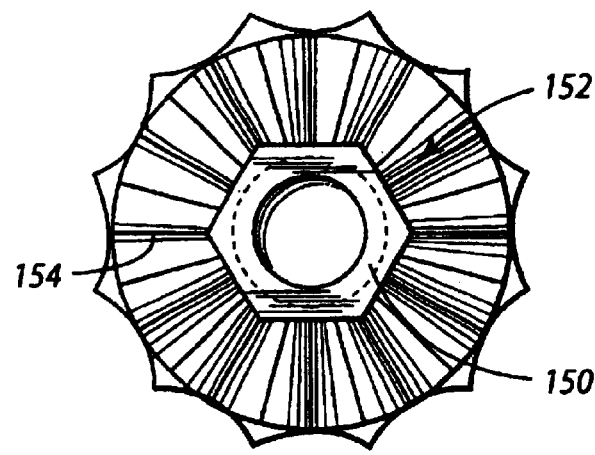
Fig. 16  Fig. 17
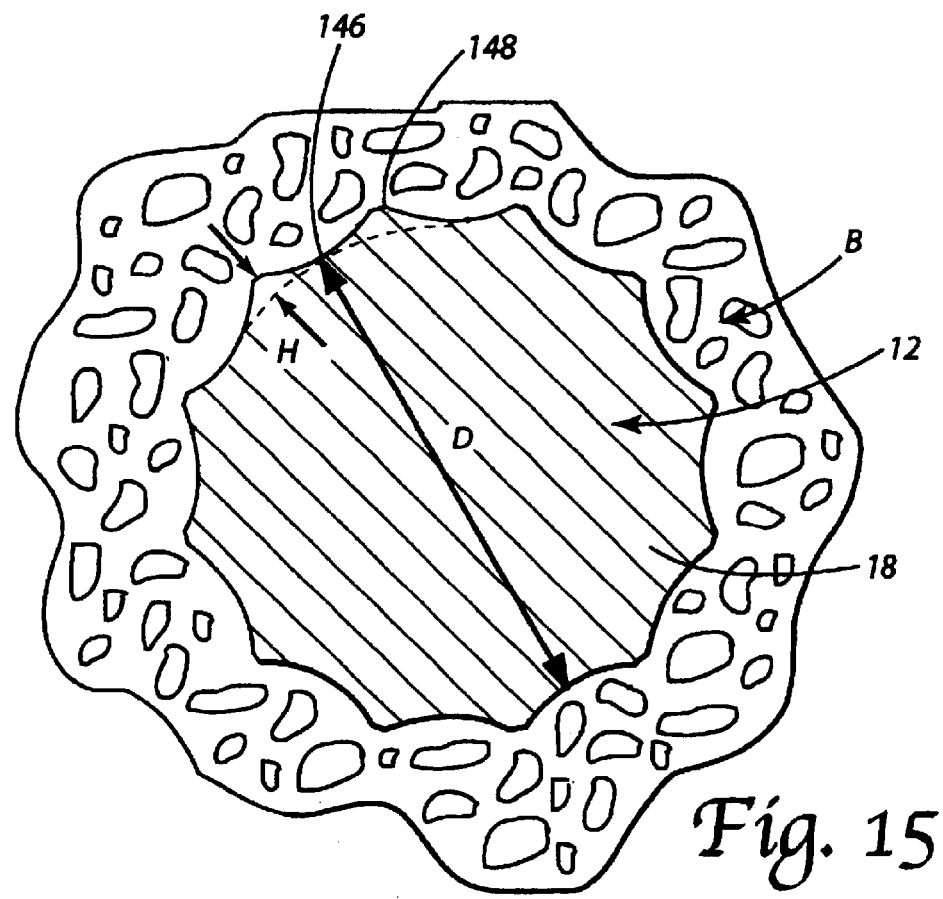
Fig. 15

DENTAL RESTORATION APPARATUS

CROSS-REFERENCE TO RELATED APPLICATIONS

This application is a continuation-in-part of application Ser. No. 08/985,675 now abandoned filed Dec. 5, 1997 and a continuation of application Ser. No. 08/986,177 now abandoned, each filed in the United States on Dec. 5, 1997, and similarly claims the benefit of Provisional Application Serial No. 60/032,827, filed in the United States on Dec. 12, 1996.

TECHNICAL FIELD OF INVENTION

The present invention is directed to developments in the dental field, with particular regard to dental restoration apparatus. Typically, apparatus of this type includes a prosthetic implant, an abutment and a fastener apparatus. In use, the implant is adapted to be implanted within an anchor site fashioned within the bone of the jaw of a patient. The abutment is adapted to be mounted on the implant to provide a support surface for a tooth restoration. And, the fastener apparatus functions when engaged with both the implant and abutment in a mounted orientation to secure the structures in a manner to positively resist relative movement of the abutment and implant both axially and rotationally.

BACKGROUND OF THE INVENTION

It is common practice in dentistry and dental surgery to use a prosthetic device characterized as an implant to serve as a base to support a tooth restoration in the process of replacing a natural tooth lost for some reason. In this practice the implant is imbedded in a site referred to as an anchor site created in the bone within the jaw of the patient. It is hoped that the implant, during a healing process, will become secured to and integrated with living bone cells juxtaposed thereto, thus becoming immobilized within the anchor site.

Implants of the prior art have been designed variously in order to achieve a level of securement during a process of biological cementation, known as "osseointegration," when the implant attaches to and integrates with living bone cells in position in situ within the anchor site. Generally, the implant includes a body formed either of circular cross-section or of gradually tapered outline from a trailing end toward a leading end. It is intended that implants fabricated in these body shapes when received in the anchor site become immobilized in the seated, final disposition to function as a final, stable and secure base for mounting an abutment and tooth restoration.

Many prior art designs of dental restoration apparatus and its component parts function adequately in carrying out the intended use. However, many designs of implant are known to suffer from a number of well documented difficulties and shortcomings that continue to require attention of those involved in the art of tooth restoration.

Many of these difficulties and shortcomings are attendant to factors including the consequences of and the reaction to the force of loading upon the implant/abutment interface during the initial or integration phase, particularly with forces such as those generated during eating, and the consequences of and the reaction to the lack of adequate surface area of the body of the implant in contact with viable tissue and bone cells within the anchor site.

Another difficulty and shortcoming has its genesis in the placement of threaded implants in dense or poorly vascularized bone, or in loose, poorly organized bone with excess fatty bone marrow. In the former, the pressure of threading an implant into a tapped, dense, hard bone may cause pressure necrosis at the implant bone interface, resulting in failure or a total loss of the implant due to bone necrosis and subsequent fibrous integration of the implant to the bone. In the latter case, implants threaded into bone of poor quality, such as loosely organized bone with fatty bone marrow generally are inadequately stabilized. The inadequacy of stabilization will subsequently lead to failure of the implant.

The body surface of the body of many implants of the prior art is smooth throughout. This is the case irrespective of whether the implant is of circular cross-section or of a configuration tapered from a trailing toward a leading end. The implant of each configuration is pressed fit into the anchor site to the final, seated disposition. Thus, the anchor site within which the body is received is specially fashioned to accommodate the implant whatever the size of the body and whatever its outline. If the anchor site is not properly sized problems will occur. For example, if the anchor site is oversized, the implant will not be supported properly during the healing process. Any movement of the implant when subjected to a force, such as a loading force acting at the implant/abutment interface during the initial healing or integration phase, or within another location during chewing or other oral functions will impede the process of osseointegration. On the other hand, if the anchor site is undersized, the body of the implant likely will cause damage to the cellular bone structure within the anchor site as the implant is pressed fit or threaded (screwed) to the final, seated disposition. Damage represented by crushed bone and fibrous tissue formation should be avoided as best as possible. Thus, the dentist or dental surgeon strives to fashion an anchor site to a size that closely tolerates movement of the implant during implantation, and presents a maximum amount of surface area within the wall of bone that ultimately will reside in intimate contact with the surface of the body of the implant. Adverse characteristics, including those that are the resultant of a poorly prepared anchor site, a poor quality of bone within the anchor site and/or any capability of movement of the implant during healing must be reduced substantially or totally eliminated.

The consequences of loading evidence themselves rather dramatically.

In the past, implants were used by dentists and dental surgeons as anchors for denture/bridge constructions for replacement of multiple, natural teeth. The prior art included implants specifically designed and generally suited for that purpose. Recently, however, dental professionals are being asked to respond to requests related to other aspects of dental surgery, namely that of replacement of individual teeth with tooth restorations that appear more like the natural tooth that was lost. Prior art implants, typically, were fabricated with a body providing only a few millimeters of interface diameter for support of a crown or other restorative structure. The range may be 4 mm or less measured between the occlusal margins. It is not unusual, however, for the dentist or dental surgeon to work with a crown or other restorative structure having an occlusal loading surface much larger in interface diameter. For example, the occlusal loading surface of a molar is in the range of about 6–7 mm by 10–12 mm. Oftentimes, failure and resultant breakdown occurs at the interface of implant and abutment. This may be evidenced by a ditching effect around the cervical margin of the implant, a resultant or associated bone loss, and a loosening or fracture of the body of the crown or tooth structure.

Still further, the emergence profile of the crown as it comes through the gum tissue generally is not aesthetically pleasing. This is because the large size of crown associated with a small diameter implant has an unnatural appearance. Furthermore, periodontal disease may develop as a result of the unnatural undercut of the relatively large crown as it tapers to meet the relatively small body of implant.

In addition, fastener assembies used in prior art to connect the implant and abutment and, then, maintain the connection so that the abutment cannot loosen itself from the condition of engagement with the implant suffer from various difficulties and shortcomings. If the fastener assembly is incapable of maintaining integrity between the abutment and implant, the prosthesis can be damaged, and possibly require replacement. In addition, the loss of integrity of the connection between abutment and implant resulting in microvibratory movement of structures and deterioration of bone cells and tissue within and around the anchor site will encourage a growth of bacteria, leading to gum disease. The effect is cervical bone loss around the neck or shoulder of the body of the implant, and ultimately bone loss along the longitudinal length of the body.

Threaded fasteners, such as screws and bolts for securing workpieces together are well known in the art and have been utilized in a wide variety of applications. Some fasteners are useful since they may be selectively secured and released, as may be required. However, many screws and bolts of this type suffer from one or more shortcomings. One shortcoming, the resultant of conditions of mechanical vibration, manifests itself by a tendency of the screw or bolt to loosen or "back out" from one or the other or both workpieces over time.

In order to address this problem, lockwashers and locknuts of well known design have been developed for use in concert with the screw or bolt. Other mechanical elements, such as a fastening element with a slotted conical sleeve disclosed in U.S. Pat. No. 4,370,082 to Sandberg, and a screw fastener with a concentrically disposed O-ring disclosed in U.S. Pat. No. 5,12,839 to Ingber et al have been developed to meet a need.

Currently available lockwashers and locknuts function effectively but they have their drawbacks. To this end, lockwashers tend to be unsightly. Accordingly, lockwashers are not suited for, and tend not to be used in, applications placing emphasis on the aesthetics of the workpiece connection. Locknuts including a nylon walled bore generally only provide reliable locking action the first time they are used. Accordingly, locknuts are not a preferred mechanical element when the fastener is to be reused.

The structure in the form of a slotted conical sleeve, disclosed in the Sundberg patent, generally is limited in use in mounting objects in hard materials such a stone, brick, plaster, concrete or the like, and holding the fastener in the material by frictional force. Again, the application or use of the conical sleeve is limited, and generally only reliably effective for a onetime use application.

Finally, the screw fastener with the concentric O-ring, disclosed in the Ingber et al patent, is not appropriate for certain applications where the resilient rubber of the O-ring would deteriorate or have a tendency to deteriorate during use in the particular environment over time.

Accordingly, a need currently exists for an improved fastener assembly providing greater versatility, reusability and a longer service life. A need also exists for an improved implant and abutment providing the same goals.

BRIEF SUMMARY OF THE INVENTION

The present invention in the field of dental implantology is considered not only to address but successfully satisfy desires and demands of the patient regarding dental restoration apparatus. To this end, the structure of the invention has been found to permit immediate or early loading of an implant once received within an anchor site in the jawbone of the patient. In addition, the structure of the invention has been found to enhance the capability of bone integration with the implant to effectively accelerate the time between placement of the implant and that of actual loading of the implant with a final restoration. Thus, the invention recognizes the desires and demands directed to the practice of dental implantology by providing an extremely stable implant and permitting early or immediate loading without resultant breakdown.

Accordingly, it is an object of the present invention to provide a dental restoration apparatus including an implant, abutment, and a fastener assembly that overcomes the shortcomings, limitations and disadvantages of the prior art briefly discussed above.

Another object of the present invention is to provide the body of an implant with a pattern including one or more projections characterized as "flutes" extending along the body of the implant to substantially increase the surface area of contact between bone tissue and implant within the anchor site. It is intended that the implant once the process of implantation is completed and the healing process runs to completion, will secure to and integrate with the bone tissue within the anchor site in a more positive manner and provide a more secure base for other components of the dental restoration apparatus. The increase in a capability of securement is considered to follow the cutting action of each flute into the wall within the anchor site and into bone tissue during pressed fitting of the implant to a final, seated position. The increased surface area from tip-to-tip along the pattern of flutes remains in contact with the bone during healing. Not only is the surface area of the body when compared with an implant otherwise of like construction increased by a factor of about 50% or more the pattern of flutes adds stability to the implant to assist in osseointegration.

A further object of the present invention is to form the body of an implant in a circular cross-section along substantially its entire surface from the trailing end to the leading end, and provide the body with a pattern of one or more flutes, as discussed in the immediately preceding paragraph. The pattern of flutes that increases the surface area of the implant permits use of an implant in a tooth restoration process is of smaller cross-sectional dimension than an implant otherwise considered for use.

Still another object of the present invention is to form the body of an implant with a leading end of a first cross sectional dimension and a trailing end with an enlarged shoulder. The structure of the implant throughout its leading end minimizes the need for bone removal within the anchor site to maximize the quantity of viable bone cells available around the anchor site. The enlarged shoulder that locates within a counterbore of less depth provides a larger surface for receiving the components of the dental restoration apparatus, to better distribute a load that may be placed upon a restorative crown during chewing.

An additional object of the present invention is to provide an improved fastener assembly including a fastener member and sleeve capable in use in connecting the other components of the dental restoration apparatus in a manner preventing movement of the components. Movement is prevented axially through mechanical compression and rotationally through a friction member acting between components.

Yet another object of the present invention is to provide a fastener assembly of relatively simple and inexpensive construction that not only is versatile but also useful in its application over an extended period of time and multiple uses.

Yet another object of the present invention is to provide a fastener assembly of the above construction appropriate for applications where the fastener member must be loosened or removed periodically. To this end, the fastener assembly advantageously functions over a long service life frictionally.

Additional objects, advantages and other novel features of the invention will be set forth in part in the description that follows. Other objects and advantages will become apparent to those skilled in the art upon examination of the text and/or realized and obtained by consideration of the instrumentalities and combinations particularly pointed out in the appended claims defining the scope of the present invention.

The preferred form of the invention in a dental restoration apparatus includes an implant having a body of substantially solid construction fabricated in a circular outline from a trailing end at a mounting surface substantially to the leading end. The implant further includes a pattern including one of more flutes along the surface of the implant extending between the leading and trailing ends in an attitude substantially parallel to an axis through the body. In the preferred embodiment, the pattern includes a plurality of flutes arranged equidistantly around the body,. Each flute includes a tip that functions as a cutting instrumentality when the implant is pressed fit into an anchor site. Each flute, therefore, cuts into the bone tissue as the implant is moved in the seating direction, and remains within the cut to better stabilize the implant during healing.

In another form of invention, the dental restoration apparatus includes an implant having a body and an enlarged shoulder at a mounting surface at a trailing end. Additionally, the dental restoration apparatus includes an abutment having a body and a mounting surface at a leading end adapted to move into a generally coplanar relation with the mounting surface of the implant. Preferably, the mounting surfaces have mating, interlocking profiles preventing relative rotation between the implant and abutment when mounted together in a positional adjusted location.

In yet a further form of the invention, the body of the implant may have a diameter of between substantially 3.5–4.0 mm and a shoulder and mounting surface of a diameter somewhat larger in size. Advantageously, the relatively small body dimension allows the surgeon to minimize bone removal within the anchor site. Consequently, a larger area of viable bone cells remain adjacent the anchor site. The shoulder of enlarged diameter is considered to support the crown and distribute the load and stress generated during mastication over a larger surface area. A radiused transition shoulder connecting the mounting surface and body also reduces stress, more evenly distributes the load and provides a stable seat for the implant that resists rocking that could otherwise lead to bone loss and loosening of the implant over time from the in situ residence position within the anchor site.

In addition, to achieve the foregoing and other objects and in accordance with the present purposes and aspects of the present invention as described herein, an improved fastener assembly is provided for engaging and positively resisting loosening from at least a pair of workpieces. These workpieces comprise an implant and an abutment of the dental restoration apparatus. The fastener assembly comprises a fastener member including a head and an elongated body extending from the head to a distal end. The elongated body has a first diametrical dimension D and is threaded over a portion of its length from the distal end toward the head. The fastener assembly also comprises a sleeve member formed of resilient material circumferentially received about the elongated body. The sleeve member includes an inner and outer surface and a slit through both surfaces from end-to-end creating opposed, spaced-apart, confronting surfaces throughout the full length of the sleeve. The diametrical dimension of the outer surface is S (wherein S>D). In addition, the fastener member includes means for compressing the sleeve member so that the sleeve compressively engages against the elongated member to bind the fastener assembly against loosening from the workpieces as the fastener member is tightened.

The compressing means may be a protuberance or series of protuberances formed on the outer surface of the sleeve member in a midpoint location between its ends. Each protuberance provides a focused pressure point to deform the sleeve from a relaxed condition and bind against the fastener member, thereby preventing loosening as a result of vibration propagated through the workpiece and the fastener assembly.

Preferably, however, the compressing means is comprised of an outward bow in the inner and outer surfaces of the sleeve member at the midpoint between its ends, around the sleeve from one confronting surface to the other confronting surface. Similarly, the outward bow provides a focused pressure point and similar action-reaction of during deformation.

In a more specific definition, the fastener member includes an elongated body that may take the form of a screw. The fastener member further includes a second portion in the form of a channel extending from a shoulder at the end of the threaded length toward the head. The channel has a diametrical dimension D1 (wherein D1<D). The inner surface of the sleeve member has a diametrical dimension S1 (wherein D>S1>D1). As the screw is tightened into a workpiece/abutment, the outer surface within the region of the protuberance/outward bow engages the wall of an aperture. This causes the sleeve member to deform and compress inwardly from a relaxed condition further into the channel and into frictional engagement along the base of the channel. The memory of the material of the sleeve member, however, exerts an outward pressure thereby pressing the sleeve member against the wall of the aperture. This frictional engagement between the sleeve member and wall of the aperture functions in conjunction with the movement of the sleeve member into the channel to provide a positive holding force that resists loosening of the fastener member.

The fastener assembly of the present invention has a long service life. The fastener member, in fact, is reusable, effectively functioning throughout its life to positively resist loosening equally well on the first and subsequent uses. Aesthetics are of no concern since the structure of the fastener member is hidden from view within the workpiece/dental restoration.

Finally, In a preferred form of the invention the fastener is formed by a member including an elongated body with a head at one end and thread extending from the opposite end toward the head. The threaded length has a first diametrical dimension. A channel of a second, smaller diametrical dimension is located between the head and threaded portion. The fastener also includes a sleeve of resilient material received within the channel. The sleeve has an inner and outer surface, and slit though the surfaces forming opposed, spaced-apart confronting surfaces. The outer surface of the sleeve has a diametrical dimension greater than that of the threaded length so that the outer surface of the sleeve in a relaxed condition extends outward of the channel. Finally the sleeve includes an outer circular bow in the outer surface to exert a force in compression to deform the sleeve into a tight frictional engagement within the channel.

Still other objects of the present invention will become apparent to those skilled in this art from the following description, claims and drawings that illustrate and describe a preferred embodiment of the invention together with the best mode suited to carry out the invention. As it will be realized, the invention is capable of other different embodiments and its several details are capable of modification in various, obvious aspects all without departing from the spirit of the invention. As such, the drawings and descriptions thereof should be regarded as illustrative in nature and not as restrictive.

BRIEF DESCRIPTION OF THE DRAWINGS

FIG. 15 is a horizontal section taken along the line 15—15 in FIG. 1;

FIG. 16 is a one-quarter horizontal section taken along the line 16—16 in FIG. 1;

FIG. 17 is a horizontal section taken along the line 17—17 in FIG. 1;

DETAILED DESCRIPTION OF THE PRESENT INVENTION

A dental restoration apparatus 10 constructed in accordance with the teaching of the present invention provides a mount for a fixed, stable tooth restoration. The apparatus comprises an implant 12, abutment 14, and fastener assembly 16 illustrated assembled together in FIG. 1, and in an exploded relationship in FIG. 2. The form of implant illustrated in FIGS. 1 and 2 may be of so-called "small body" or "large body" construction. Modifications of that implant are illustrated in FIGS. 10 through 13. Each implant illustrated in the latter figures may be specifically characterized as "large body" in construction.

The characterizations "small body" and "large body" follow from a recognition of the cross-sectional dimension of interacting mounting surfaces disposed at the trailing end of implant 12 and the leading end of abutment 14 measured at the occlusal margin, and the capability of the surfaces functioning without breakdown under occlusal forces developed during mastication. These constructions will be discussed in detail as the description continues.

All structures and modifications described herein are considered to reside within the spirit and scope of the present invention. In addition, all structures and modifications of the dental restoration apparatus, including the various component parts, are considered to be an improvement over prior art structures in that they provide a more natural, more predictable tooth restoration. In addition, the structures and modifications are considered to have improved biomechanical design characteristics to enhance the capability of integration of the implant with bone cell tissue.

Figure 1:
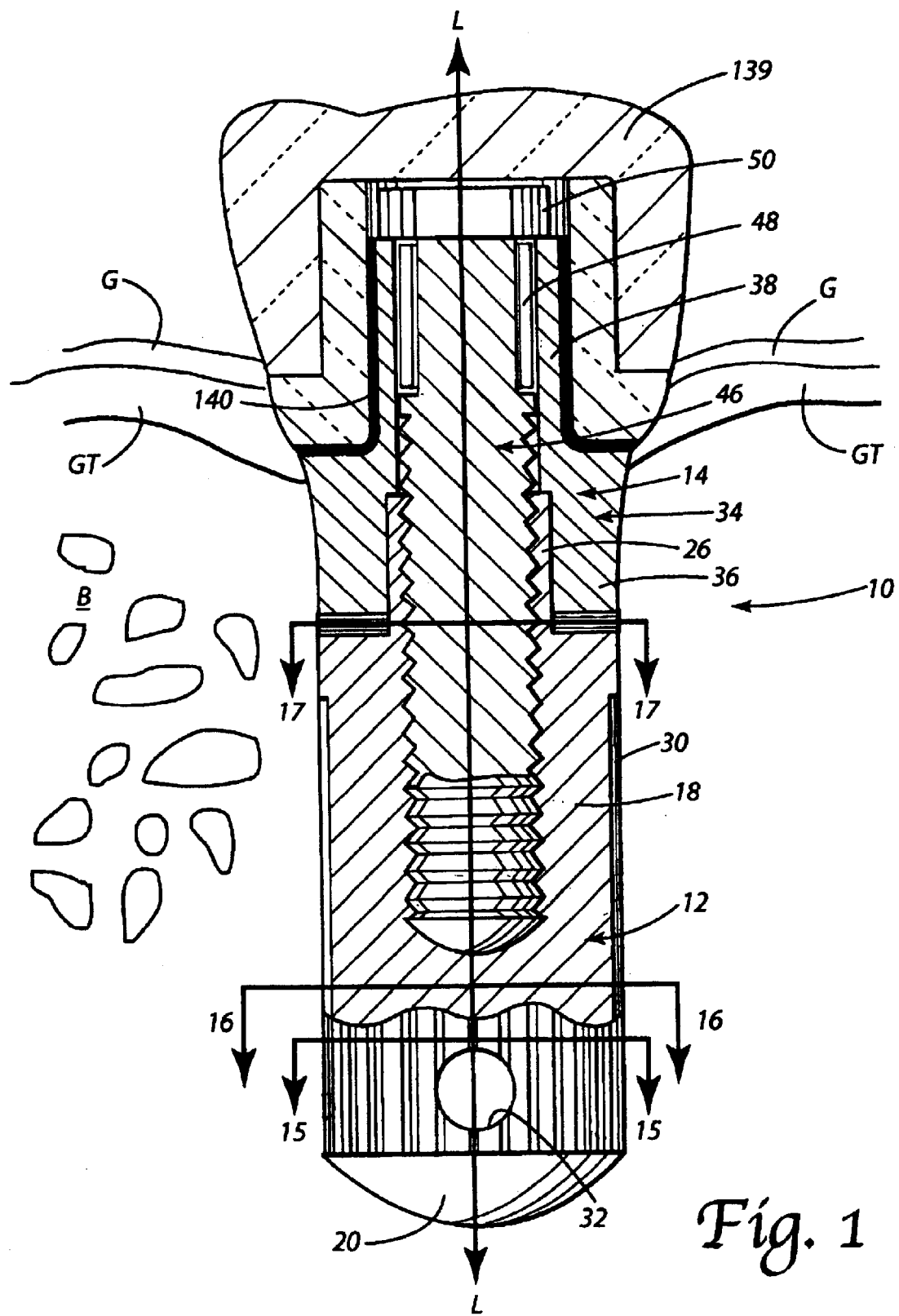
FIG. 1 is a view in elevation and partially in vertical section of the dental restoration apparatus of the invention.
Figure 2:
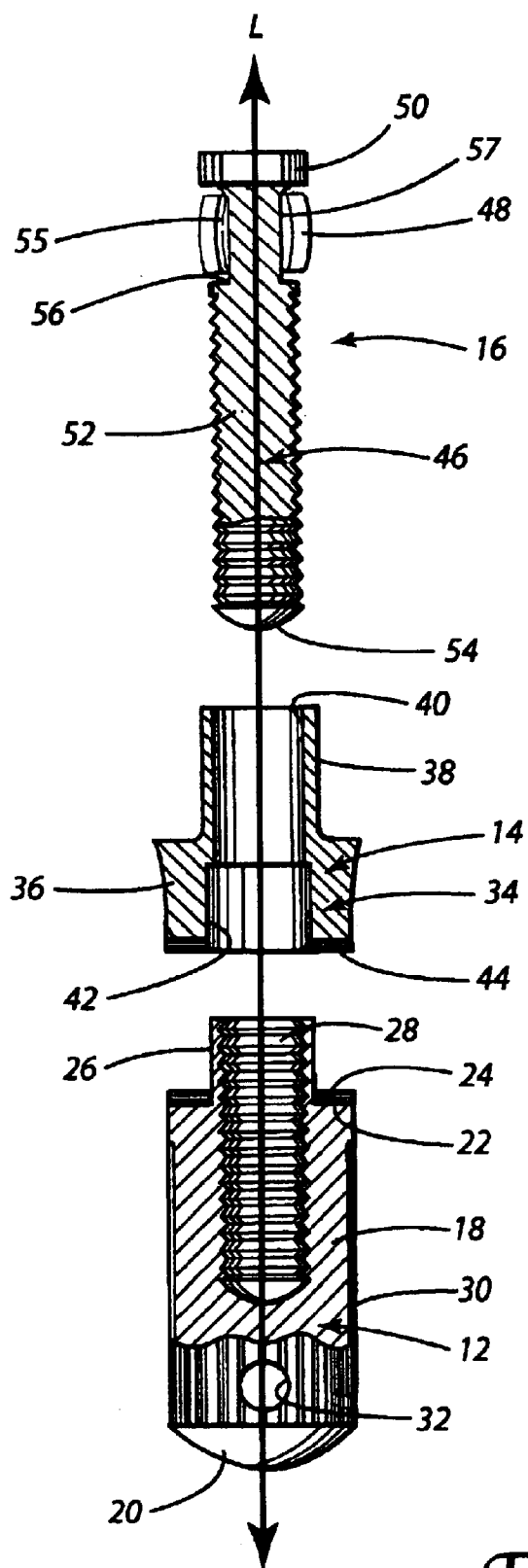
FIG. 2 is a view similar to FIG. 1 with the major component parts of the dental restoration apparatus in exploded relation.

Referring now to FIGS. 1 and 2, implant 12 comprises a body 18 having a leading end 20, a trailing end 22 defining a mounting surface 24, and a neck 26 extending from trailing end 22 away from body 18. Body 18 may be fabricated in many, different shapes, including one that is circular in cross-section. Neck 26 likewise may be fabricated in different shapes, and the neck may extend from the trailing end of body 18 in different attitudes relative to an axis, such as axis L, through dental restoration apparatus 10 and its component parts. As illustrated in FIGS. 1 and 2, neck 26 is circular in cross-section and extends from body 18 along its axis.

Throughout the description reference to "an axis" or "the axis" should be considered, unless specified otherwise, the axis of the component under discussion.

The construction of mounting surface 24 will be discussed later in the description. At this time, suffice it to say, mounting surface 24 of implant 12 includes some characteristic of irregularity throughout its overall surface area. Also, suffice it to say, the surface irregularity is complementary to a surface irregularity throughout the mounting surface of abutment 14, also discussed later in the description. The complementary surface irregularities on both mounting surfaces are designed to provide implant 12; and abutment 14 better stability when mounted together. The complementary surface irregularities also "lock" the structures precluding movement rotationally when connected together by fastener assembly 16. The more rigid connection of structures prevents problems that are chronic and of concern to the dentist and dental surgeon, such as those resulting from vibration and shimmy.

The practice of implantology as performed by dentists and dental surgeons may be carried out using an implant, such as implant 12, formed of metal or a metal alloy. Implant 12, also, may have substantially a solid cross-section throughout.

One metal used in the prior art by dentists and dental surgeons is the precious metal of pure titanium. Actually, titanium has been considered the ideal metal for use in the practice. This consideration, quite possibly has its genesis in the recognition that titanium provides particularly advantageous characteristics. One characteristic of titanium is that it is biocompatible with human tissue fluids and inert to the corrosive actions that they cause. It is also recognized, that an implant fabricated of titanium is able to provide the necessary level metallurgical strength in reaction to stress and load transfer during eating required of an implant used in an implantation process. Titanium, however, does not lend itself very well to typical prior art processes of fabrication, such as vacuum-casting or pour-casting.

Accordingly, because of fabrication difficulties, dentists and dental surgeons with increased frequency resorted to the use of alloys in the fabrication of dental restoration apparatus. One alloy commonly used is the titanium alloy referred to as "Tivanium" (composed of titanium-6-aluminum-4-vanadium). Another alloy, also comprising one of the precious metals, is "Vitallium" (composed of chromium—cobalt or vitallium).

The use of one or the other of the two alloys was found not to be a panacea and remedy for problems in prior art tooth restoration procedures. To this end, it was discovered that "Tivanium," to some degree, is subject to attack through a corrosive interaction in human tissue fluids, albeit at a level or amount of interaction that is less than the level or amount of interaction displayed by other alloys. Dentists and dental surgeons are well aware of the fact that any significant corrosive interaction between the material of the implant and human tissue fluid should be avoided, if at all possible, since a corrosive interaction directly effects the capability of the implant attaining a satisfactory level of attachment through the integration with the bone tissue during and following the healing process. They were, also, clearly aware of the fact that failing a satisfactory level of attachment, the implant will not function reliably in supporting the tooth restoration. As such, the use of alloys in the fabrication of an implant began to lose favor.

Accordingly, the body 18 of implant 12 is solid and comprised of pure titanium metal machined to the desired outer configuration. Finally, a titanium plasma spray is applied to the exposed surface area as a titanium plasma. Alternatively, titanium ion beam implantation may be applied to the exposed surface area as an ion beam plasma. As a further alternative, the titanium ion beam implantation may be applied in a process step to an open cell reticulated metal. It is believed that the reticulated metal having a controlled cell-pore-size, for example, of about 250 micrometers will assist in rapid vascular and collagen tissue growth encouraging bone formation along the body of the implant and enhance the capability of attachment of the implant to living bone tissue. In addition, many of the biologic elements which encourage bone formation may also be applied directly to the surface of the implant.

With continued reference to FIGS. 1 and 2, a bore 28 is formed along the axis. The bore extends through neck 26 into body 18. The bore is formed to a depth determined by various physical characteristics of implant 12, including that of length of the body of the implant predetermined for use by the dentist or dental surgeon in carrying out the implantation process. Bore 28 preferably is threaded along its full length, and provides a threaded interconnection between the threads within the bore and the threads of a fastener member of fastener assembly 16 used to connect implant 12 and abutment 14 when the structures are mounted together.

Finally, a pattern of flutes comprised of one or more individual flutes 30 is formed on the outer surface of body 18. Each flute 30 extends along body 18 in an attitude substantially parallel with the axis from a location spaced from mounting surface 24 to a location at or within leading end 20. As discussed below, each flute 30 of the pattern of flutes increases the surface area of body 18 of implant 12 exposed to bone cells within an anchor site. The summation of all incremental increases maximizes for any specification of implant construction the area of the surface of body 18 to which the bone tissue may adhere and integrate during the healing process.

Each flute 30 of the pattern of flutes acts as a cutting instrumentality to cut into bone tissue as the implant is pressed fit into the anchor site. Each cut into bone tissue within the wall forming the anchor site assists in creating a more stable union between the implant and the wall of the anchor site within jawbone B during a healing phase. As such, substantially all micro-movement of the implant that oftentimes prevents good bone formation against the implant may be prevented. The result is an enhanced capability to achieve the aforementioned goals.

FIGS. 15 and 16 illustrate a pattern of flutes including flutes 30 carried by a body 18 of implant 12. In FIGS. 15 and 16 the pattern of flutes includes a plurality of twelve (12) flutes arranged equidistantly around body 18 of implant 12. Patterns of flutes including an additional number of flutes similarly arranged may be considered for use, as well.

As apparent, each flute 30 is comprised of a pair of side surfaces 142, 144. The side surfaces 142, 144 each are located along an arc of curvature between a point 146 on the surface of body 18 of implant 12 and a tip 148 of flute 30. Each tip 148 may have a flattened surface or a surface substantially of knife-edge characteristics. Both forms of tip are contemplated within the spirit and scope of the invention. However, a tip 148 having a flattened surface is preferred for reasons set out below.

In FIG. 15, the diametrical dimension of body 18 is illustrated as D and the height of tip 148, measured from point 146, is illustrated as H. In FIG. 16, the width of tip 148 is W. The dimensions may be, as follows: D equals about 6 mm; H equals about 0.12 mm; and W equals about 0.3 mm.

The pattern of flutes tends to maximize for each construction of implant the surface area of body 18 exposed to bone tissue surrounding the implant within its anchor site. The increase in surface area becomes evident when data using features of both Implant No. 1 (a body of smooth surface construction having a diameter of 6 mm, and a length of 13 mm) and Implant No. 2 (a body having a pattern of flutes, and the same diameter and length) is compared.

Implant No. 1 has a circumference C of $2\pi r$, and an area A of $C \times L$.

Thus, $C = 2 \times 3.1416 \times 3 \text{ mm} = 18.85 \text{ mm}$

And, $A = C \times L = 13 \text{ mm} \times 18.85 \text{ mm} = 245.05 \text{ mm}^2$ On the other hand, assume a body of an implant with the same dimensional characteristics and a pattern of twenty-five (25) flutes (No. 16 pitch and a curvature of 0.81 mm extending to a tip whose flattened surface has a width of 0.30 mm.)

Implant No. 2 has a circumference C of 25 times the summation of length of curvature plus width of each flattened tip.

Thus, $C = 25 \times (0.81 \text{ mm} + 0.30 \text{ mm}) = 27.75 \text{ mm}$

And, $A = 13 \text{ mm} \times 27.75 \text{ mm} = 360.75 \text{ mm}^2$

It follows, therefore, that the total surface area of the body of Implant No. 2 is about 47% larger than the surface area of the body of the body of Implant No. 1.

The amount of increase of surface area of an implant, like Implant No. 2, is dependent on the number of flutes in the pattern of flutes. Accordingly, it is expected that implant 12 having the pattern of twelve (12) flutes, illustrated in FIGS. 15 and 16, will display an increase in surface area somewhat less than 47%. On the other hand, it is also expected that an implant with a pattern of flutes in excess of twenty-five (25)

flutes, but less than some maximum, upper limit, will display an increase in surface area somewhat greater than 47%. As apparent, an implant with a body of circular cross-section smaller than that of another implant may be used in replacement for the latter when the body of the former implant supports a pattern of flutes that substantially increases the surface area of the replacement.

An opening 32 or a plurality of openings formed in body 18 is also expected to increase the surface area exposed to bone cells within the anchor site by some additional amount. Each opening 32 is located within the region of the leading end of body 18 (see, for example, FIGS. 1 and 2). Each opening, further, may take the form either of an impression in the surface of the body or entry to a passage penetrating the body from one surface to an opposing surface. Each opening, further still, preferably is located at substantially equidistant spacing around body 18.

Abutment 14 is of composite construction including an interior substructure in the form of a body 34 formed about an axis. Body 34 includes a shoulder 36 at a leading end and a neck 38 extending from shoulder 36 at the trailing end. Body 34 preferably is solid in construction and fabricated of the material chosen for fabricating implant 12, discussed above.

A bore 40 coaxial along the axis extends through body 34 from shoulder 36 at the leading end to and through neck 38 at the trailing end. Bore 40 is countercut within the region of shoulder 36 throughout a length sufficient to accommodate the length of neck 26 of implant 12 when abutment 14 is mounted on the implant. The countercut is identified by the numeral 42. In the mounted position, mounting surface 44 on the leading end of abutment 14 will locate in surface-to-surface contact with mounting surface 24 on the trailing end of implant 12. The composite of abutment 14 also includes a prepable member 135 mounted on body 34 in a position around neck 38 and against the surface of shoulder 36 opposite mounting surface 44 (see FIG. 1). In FIG. 2, only body 34 of the composite construction of abutment 14 is illustrated.

The prepable member 135 may be formed of different material now in general use in restorative dentistry including various resins and porcelains. According to the invention, however, the prepable member 135 is formed of Artglass®, a trademark product of Heraeus Kulzer, Inc. of Irvine, Calif.

Artglass is a polymer glass material commonly used in restorative dental practice. Many reasons dictate this use. To this end, the prepable member 135 formed of Artglass is very easily prepared, handled and worked by the dentist or dental surgeon in an office environment. The material, also, can be added in substantially any volume to the material forming a pre-existing prepable member 135 in the event that circumstances dictate enlargement or an alteration in shape for any reason. Artglass is also aesthetically pleasing in appearance and the manner of mounting the prepable member 135 will hide from view what may otherwise be an unsightly looking body 34 of the abutment composite. In the mechanical sense, Artglass is more forgiving under loading conditions than other prepable materials, such as the resins including enamel and porcelain materials, known to the art. Finally, it is believed that the prepable member 135 formed or Artglass will provide additional protection to implant 12 with a suprabony "psuedo periodontal ligament."

As indicated, prepable member 135 serves as an overlay for body 34 of abutment 14 within the region of the trailing end. To this end, when abutment 14 in composite form including body 34 and prepable member 135 supported at the trailing end is mounted on implant 12 the interface between structures is defined by mounting surfaces 24, 44 formed of like metal located in juxtaposed relation. The particulars of the mounting surfaces will be discussed below.

A bonding agent providing an extremely strong bond is used to secure prepable member 135 in the mounted position on shoulder 36 and around neck 38. many anaerobic adhesives may be used, and Kevloc®, also a trademark product Heraeus Kulzer, has been found to provide good adhesive characteristics. Whatever the choice of adhesive, it is important that the adhesive form a stable bond to unitize the components, one to the other. As illustrated in FIG. 1, prepable member 135 may be secured in the mounted position by application of a coating of adhesive in the form of a layer 140 applied to one or the other or both confronting surfaces.

It was indicated heretofore that neck 26 of implant 12 is cylindrical in cross-section. This is the construction illustrated in FIGS. 1 and 2. The neck, however, may be modified in construction like the construction of implant 152 fabricated with a neck 150 of hexagonal cross-section (see FIG. 17). It follows that the countercut within the abutment (not shown in FIG. 17) will have the same cross-section if the abutment is to be mounted on implant 152.

A neck on an implant having a non-circular cross-section may provide the benefit of substantially unitizing or locking implant 152 and the abutment when mounted together against any relative rotational movement. Under these circumstances, the mounting surfaces, such as mounting surfaces 24, 44 simply may be flat surfaces. That construction, however, gives rise to a somewhat negative aspect, namely that the implant 152 and abutment may be mounted with only a limited capability of adjustment rotationally. Actually, the neck 150 of implant 152, if hexagonal in cross-section will receive the mounted abutment in any one of six (6) effective positions. Oftentimes, it may be critical to mount the components in a rotational attitude significantly smaller in angular adjustment. While not illustrated in the drawing, an implant may also be fabricated with a socket, configured as an analog of neck 150, extending along the axis from the mounting surface. The socket would extend throughout a length equal to the length of a neck, configured as an analog of the counter-bore, extending from the mounting surface on the leading end of an abutment.

The structures of the socket and neck, referenced to FIG. 17, are hexagonal in cross-section. The structures, additionally, may be circular or of some other cross-sectional outline. As previously discussed, outlines of circular cross-section require some characteristic of irrectuarity within the surface planes of the respective mounting surfaces, like mounting surfaces 24, 44, to immobilize the structures rotationally.

Preferably, therefore, implant 12 and abutment 14, illustrated in FIGS. 1 and 2, include a neck 26 and counterbore 42, respectively, both of which are circular in cross-section. In this adaptation of the invention, mounting surfaces 24, 44 are formed with some form of complementary pattern. For example, each surface 24, 44 may present a pattern including one (1) or more projections 154 generally of V-shaped cross-section, also see FIG. 17. Each projection of the pattern extends radially outward from the axis of the implant and abutment, respectively, to the occlusal margin. Typically, the pattern of projections within each mounting surface 24, 44 will include a multiple of projections each providing a stop against rotation of the implant and abutment in the mounted orientation. An increase in the number of projections or stops within the pattern of projections, for example, to three hundred sixty (360) projections, provides a 1° incremental adjustment of the abutment on the implant. The adjustment capability may become an important consideration when mounting the structures.

Figure 18:
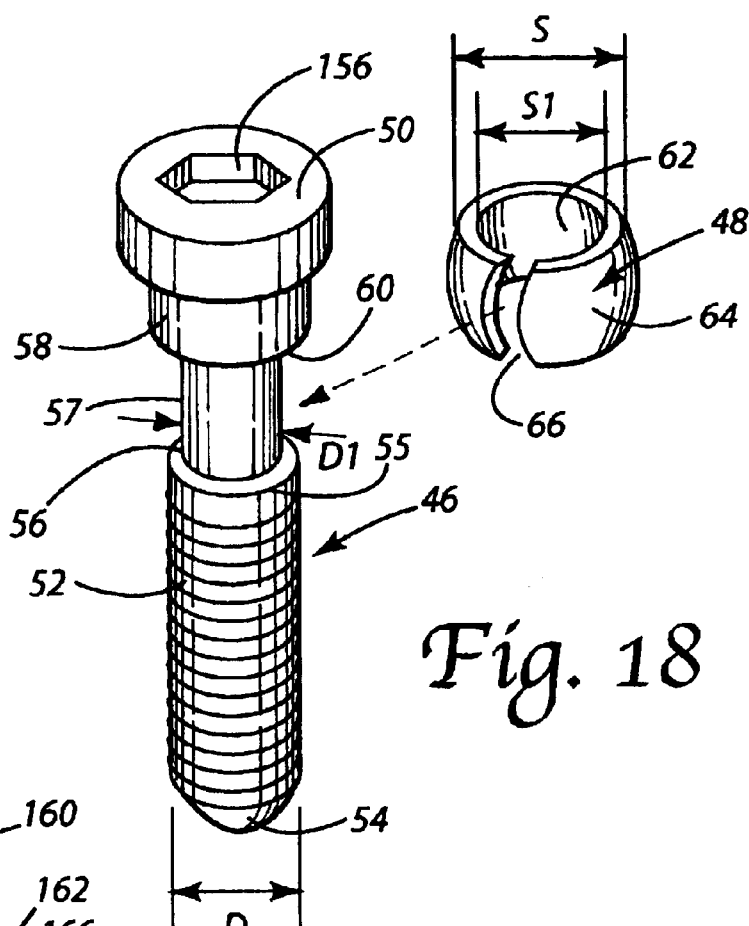
FIG. 18 is a perspective view of a fastener assembly illustrating a sleeve of the assembly exploded away from a seated position.

Fastener assembly 16 is illustrated in FIGS. 1 and 2, but likely is best illustrated in FIG. 18. Fastener assembly 16 includes a fastener member 46 and a sleeve 48, both of which are important integral parts in connecting implant 12 and abutment 14 when the structures are mounted together.

Fastener member 46 may take the form of a screw, bolt or other equivalent fastener structure including a head 50 and a body 52 extending from the head along the axis toward a leading end 54. Body 52 is threaded from the leading end 54 throughout a length sufficient to interact in and along the threaded length of bore 28 when connecting abutment 14 to implant 12.

As illustrated in FIG. 18, the threaded portion along body 52 extends from leading end 54 to a collar 55 and shoulder 56 spaced from head 50. A second collar 58 and shoulder 60 extends from the undersurface of head 50. Shoulders 56, 60 are located in opposed relation, spaced apart a distance sufficient to provide a mounting surface for supporting sleeve 48 when it is mounted on body 52. The mounting surface may define a channel 57 of circular cross-section.

The undersurface of head 50 surrounding body 52 may serve equally well as the second collar and shoulder combination (see FIGS. 1 and 2). In either form of the invention, channel 57 extending from shoulder 56 may merge directly into shoulder 60 (see FIGS. 1 and 18) or it may merge into shoulder 60 in a slightly chamfered attitude (see FIG. 2).

Sleeve 48 includes inner and outer surfaces 62, 64. A slit 66 is cut through both surfaces from one end to the other. Both inner surface 62 and outer surface 64 are bowed outwardly from the region of the ends of sleeve 48 to substantially a midpoint location. In the relaxed condition, sleeve 48 has a length dimension at least equal to the distance between shoulders 56, 60, each of which provide support for at least a portion of the ring surfaces at the respective, opposite ends of sleeve 48.

Fastener member 46 may be formed of metal, metal alloy, a composite, rubber, a synthetic plastic material, or nylon. Preferably, however, the fastener member 46 is formed of the same material chosen in the fabrication of implant 12 and abutment 14. The selection of like materials in fabricating the components of the dental restoration apparatus 10 obviates any tendency of expansion/contraction of materials at different rates, as expected when materials with different coefficients of expansion/contraction are used. Sleeve 48 is formed of a resilient material, such as titanium.

According to a representative embodiment of the invention, body 52 and collar 58 of fastener member 46, assuming fastener member 46 includes a collar, may have a diameter D. Channel 57 may have a diameter D1 (wherein D>D1). Inner surface 62 of sleeve 48, at the location of a ring surface may have a diameter S, and the outer surface 64 of sleeve 48, also at the location of a ring surface, may have a diameter S1 (wherein S1>S, D1<S<D, and S1>D).

Figure 19:
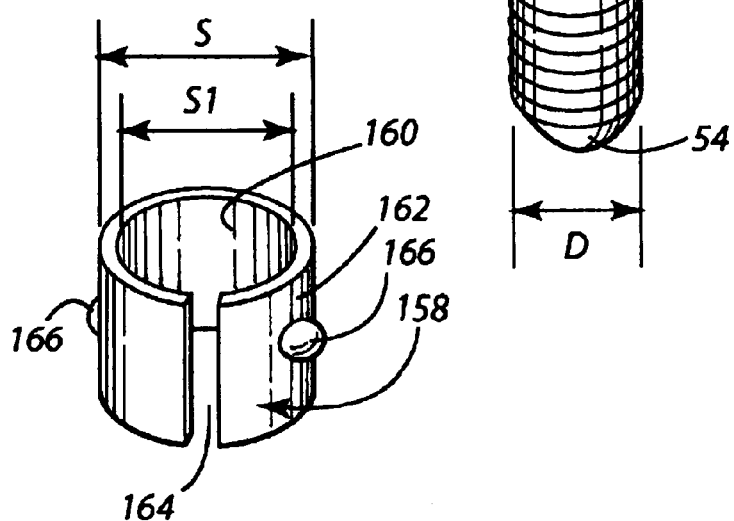
FIG. 19 is a perspective view of a sleeve of modified form.

A sleeve 158, comprising a second form of sleeve, is illustrated in FIG. 19. Sleeve 158 may be used in replacement of sleeve 48 of fastener assembly 16. Similar to the sleeve initially described, sleeve 158 includes inner and outer surfaces 160, 162, and a slit 164. Slit 164, also, is cut through both surfaces from one end to the other. Inner and outer surfaces 160, 162, unlike the surfaces of sleeve 48, are disposed substantially along concentric circular planes. A protuberance 166 is located within the outer surface within a mid-length region. Preferably, however, a plurality of protuberances 166 will be disposed equidistantly around sleeve 158 at the mid-length location. The protuberances extend from the outer surface through a distance substantially equal to the distance of the outward bow of inner and outer surfaces 62, 64 of sleeve 48.

In a relaxed condition, sleeve 158 has a length dimension at least equal to the distance between shoulders 56, 60. As discussed, each shoulder provides support for at least a portion of the ring surfaces at the respective opposite ends of sleeve 158.

Sleeve 158 may have the dimensions heretofore described in the description of sleeve 48, and the same relative dimensions as described in the description of fastener member 46. Sleeve 158, also, may be formed of the same material used in the fabrication of sleeve 48.

Implant 12 and all other implants disclosed herein are adapted for receipt within an anchor site cut by the dentist or dental surgeon into the jawbone B of a patient. It is intended that each implant serve as a replacement for the root portion of a natural tooth lost for whatever the reason. Thus, it is intended that each implant once the healing process is completed function as an anchor or footing within jawbone B for support of the implant and other components of the dental restoration apparatus, and the tooth restoration. If the restorative process is to attain that goal, each implant over time must attach biologically to the cells of bone with which it is in contact. The process of biological cellular acceptance and attachment between bone cells and the body of the implant exposed to the bone cells that it contacts is referred to as osseointegration. For the process to run to conclusion, and run successfully, several factors must be observed. These factors, among others, include the following:

1) The material of the implant must be inert to and passive within body tissue fluids;
2) the surface of the implant prior to use must be sterilized, and remain in a sterile condition during the implantation process;
3) instrumentation preferably fabricated of the same material as the implant should be used to grip the implant during movement leaving the implant devoid of all foreign material; and
4) the anchor site must be prepared carefully, with as meticulous an approach as possible in order to attain a satisfactory fit between the body of the implant and the bone cells within the anchor site cut in jawbone B.

The practice of implantation now carried out by dentists and dental surgeons for all intents and purposes has followed one of two generally recognized processes. One process is implemented in a so-called "two-stage implantation technique" illustrated by the sequence presentations of FIGS. 3 through 8.

Figure 3:
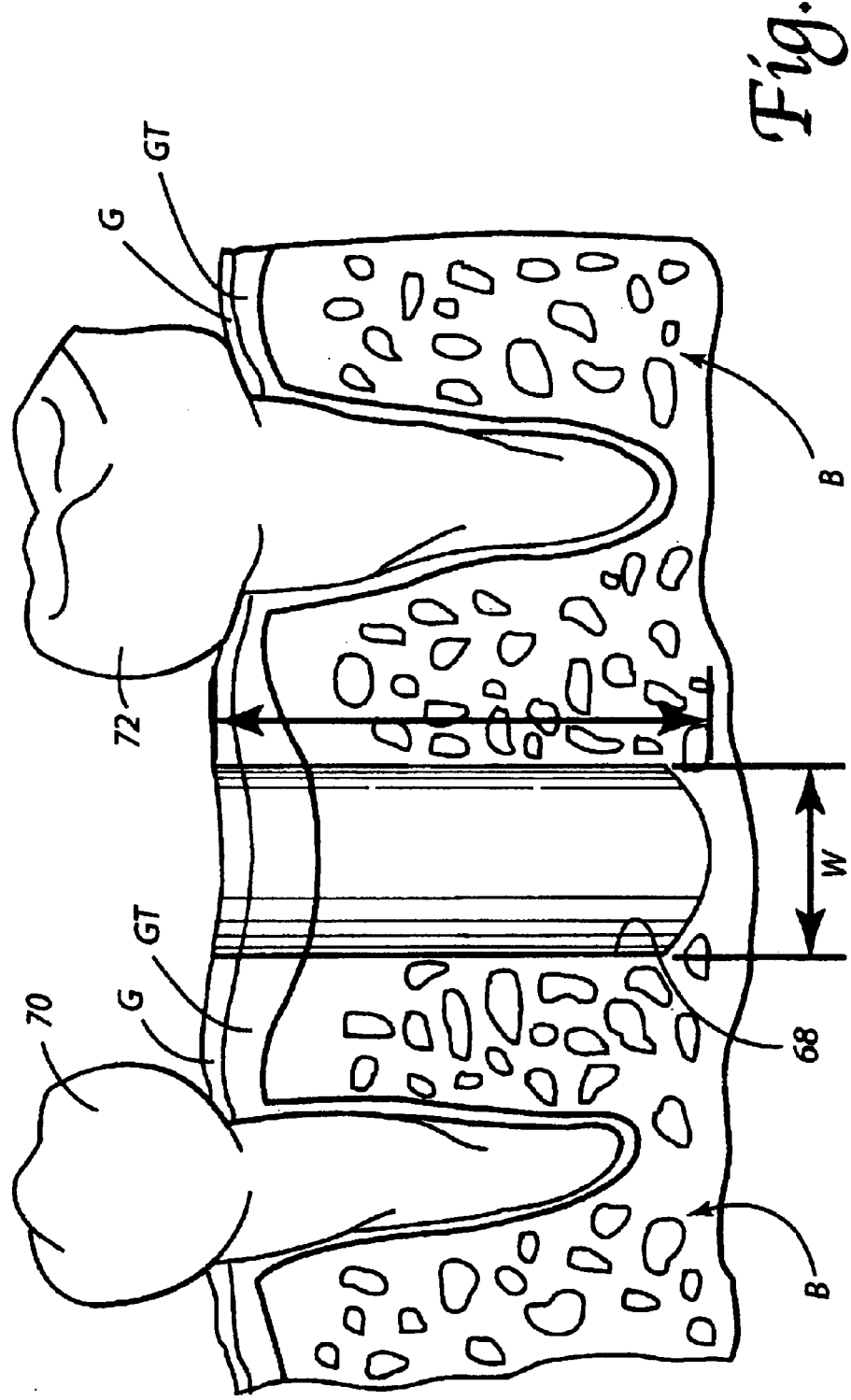
FIGS. 3 through 8 are schematic views of the jawbone within an oral cavity illustrating the site for placement of a tooth restoration and typical steps in carrying out a dental restoration technique.

Referring to FIG. 3, the dentist or dental surgeon first prepares anchor site 68 at an appropriate location between a pair of existing, natural teeth 70, 72. Anchor site 68 may be cut into jawbone B after opening the site and exposing its location by introduction of a surgical cut through gum G and gingival tissue GT. The cut to create anchor site 68 is made slowly by implementation of hand-held boring/drilling equipment, such as an electric-driven or air-driven, slow speed, handpiece designed to provide control at a high speed of 5000 rpm and a low speed of 15 rpm. During cutting, as indicated, copious amounts of liquid, such as water, are introduced to the anchor site to assist in prevention of any heating of bone cells, particularly to temperatures above about 42 to about 47° C. The liquid also assists in proper management of bone cells within or adjacent to the anchor site so they will not be destroyed with associated cellular tissue either by trauma or heat generated during surgery. It is hoped that the process will promote more natural healing and better bone integration to implant 12 within the anchor site.

Anchor site 68 is cut preferably in a cylindrical outline to a depth sufficient to accommodate the full length of body 18 of implant 12 when the implant is located in a fully seated disposition. Thus, when implant 12 is fully seated, see FIG. 5, it is intended that only neck 26 extend beyond the entrance to anchor site 68. Preferably, neck 26 will extend, only, to a location below the level of gum G, within the layer of gingival tissue GT.

The dentist or dental surgeon may cut anchor site 68 substantially to any depth D, and any width W. For example, anchor site 68 may be cut to a depth within a range of depths that vary from a minimum of about 4 mm to a maximum of about 15 mm. Anchor sites having depths within the range of, for example, 7 mm, 10 mm, and 12 mm are also common. Regarding the criteria of width, anchor site 68 may be cut to a width W of about 3 to about 4 mm, or possibly to a width of about 6 mm. The width of anchor site 68 typically will be dimensioned slightly less than the width of the implant chosen for implantation. For example, an anchor site 68 cut to a diameter of 6 mm will receive implant 12 having a diametrical dimension of 6 mm increased by a small increment that may be on the order of about 0.25 mm. The overall measurement is taken at an outermost point at the tip of a flute of a family of flutes carried by the body, or the outermost surface on a pattern of threads. Preferably, the cross-section of an implant having a smooth body construction will be substantially equal in diametrical dimension to that of the anchor site.

An implant with a pattern of flutes is pressed fit into anchor site 68, whereas, an implant with a pattern of threads is threaded into anchor site 68. In both instances, the wall of the anchor site is cut by either a flute or a thread, and each flute and thread will remain in situ substantially within the wall surface that it cuts, increasing by some factor the degree of stabilization of the implant within the anchor site.

The width dimension of the body of an implant generally has been the characterizing feature in classification of an implant as a so-called "small body" implant as opposed to a "large body" implant. The "small body" implant typically includes implants having a body whose diametrical dimension at a mounting surface measured at the occlusal margin is about 4 mm or less. The so-called "large body" implant, discussed in greater detail as the description continues, typically includes an implant whose diametrical dimension within the region of the mounting surface is greater than that of the "small body" implant possibly by as much as 2 mm.

Implants of the so-called "large body" variety are illustrated in FIGS. 10 through 13. As may be apparent, the body of each implant illustrated in the figures distinguishes from implant 12 in that it includes a shoulder at the trailing end of the body having a diametrical dimension larger than that of the body.

Implants of so-called "small body" size have been used in anchor sites cut within jawbone B at a host of locations throughout the oral cavity. For example, if the anchor site is located in the back areas of the upper and lower jaws, in the location of the molars the implant must be capable of support of a molar having an occlusal surface area that typically may be on the order of about 6 to 7 mm by about 10 to 12 mm. Typically, an implant having a mounting surface providing a loading interface of 4 mm between the implant and abutment is capable of support in reaction to the forces applied by the molar during mastication, if the forces are applied vertically. However, when the forces applied are applied against the mounting surfaces in directions other than vertical a condition of break down oftentimes occurs within the mounting surfaces at the implant/abutment interface. The problems of break down become a particularly acute problem when the implant is of so-called "small body" construction.

Break down may be evidenced by vibration and shimmy of the implant within the anchor site, leading to a failure of the implant to bond with the bone cells. The failure to bond creates a so-called "ditching effect" that occurs around the cervical margin of the implant, with associated bone loss. In addition, abutment and implant crowns frequently loosen or fracture from the underlying implant. Further still, the aesthetic emergence profile of the crown penetrating the gum tissue is not pleasing. The consideration of aesthetics may have its genesis in a difference of size of structures, such as that of the crown relative to the mounting surface of the implant. Finally, periodontal disease may develop because of the unnatural undercut of a large crown that tapers into the "small body" implant.

Recently, however, dentists and dental surgeons have attempted to overcome problems resulting from use of a "small body" implant. To this end, the dentist and dental surgeons have resorted to cutting anchor sites to a larger diametrical dimension, for example, of 6 mm to accommodate the implant of so-called "large body" size. It is important, however, that the dentist or dental surgeon consider various circumstances attendant to use of the "large body" construction of implant. To this end, it is important to consider the necessity of management of viable bone tissue within which the implant "lives" thereby to maintain the viable bone tissue at a level of greatest volume possible to support the implant and maximize the living environment. As likely apparent, many factors are considered in determining the diametrical dimension of the anchor site. Among others, the factors include a consideration of the location of the anchor site within the oral cavity, and a consideration of the amount and integrity of bone within which the dentist or dental surgeon must work in fashioning the anchor site. In addition, the dentist or dental surgeon must consider requirements in the size of the loading occlusal surface area and provide against fracture and mechanical breakdown within various interfaces of implant, abutment, and tooth restoration. Implant 12, as discussed, is representative of either the so-called "small body" or "large body" implant and characterizes the preferred form of implant of the present invention.

Figure 4:
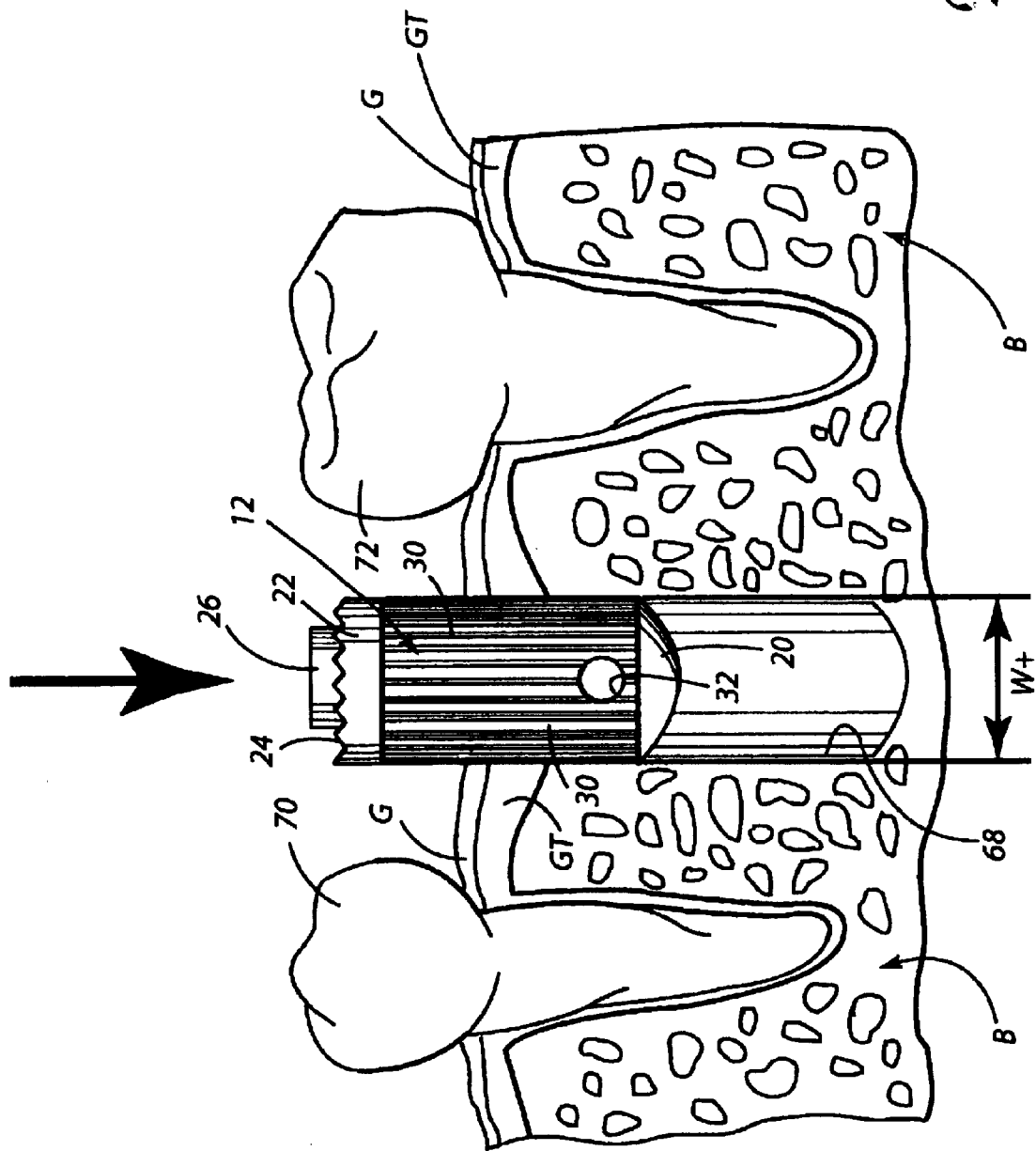
Figure 5:
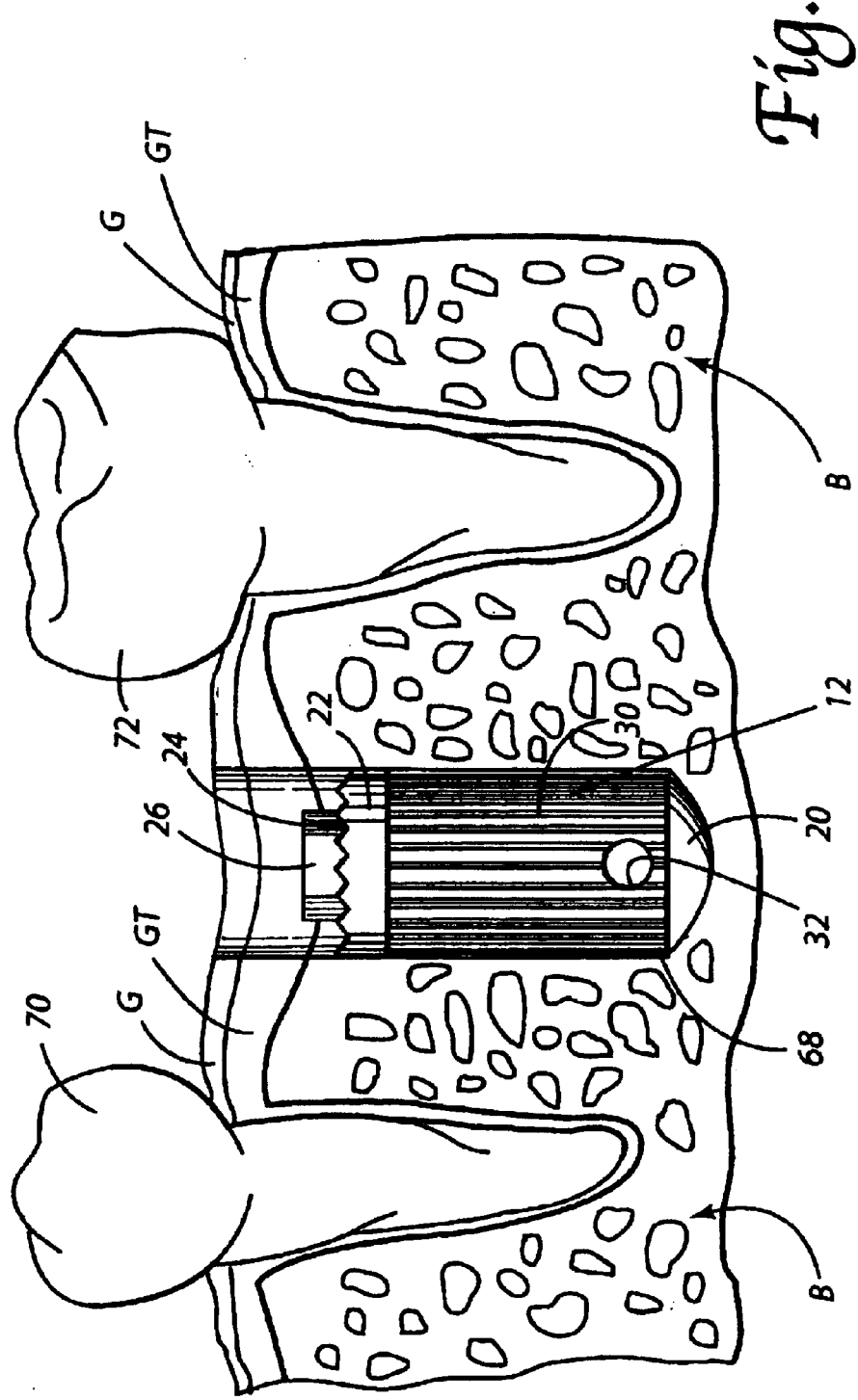

Continuing with the discussion of the "two-stage implantation technique," with reference to FIG. 4, implant 12 is illustrated in a position of partial receipt within anchor site 68. Implant 12, then, is pressed fit in the direction of the arrow to a fully seated position illustrated in FIG. 5. Any manner or means used by the dentist or dental surgeon to impart movement to implant 12 within the concepts of the factors, above, may be employed.

With further regard to FIG. 4, it should be noted that implant 12 includes a pattern of flutes 30, and that the overall diametrical dimension of body 18 is somewhat larger than the diametrical dimension of anchor site 68. The diametrical dimension of body 18 of implant 12 is illustrated as W+. As indicated earlier, the incremental increase is on the order of about 0.25 mm for a so-called "large body" implant. The increase may be somewhat less than 0.25 mm under circumstances that the implant is of "small body" variety. Tolerance considerations are not extremely critical when using an implant having a pattern of flutes, or a pattern of threads. To this end, as discussed above, each flute or thread within respective patterns acts as a cutting agency cutting a path within the wall of the anchor site axially during movement to a seated position. However, tolerance considerations are important regarding a depth of cut because the cut into the bone/tissue should result only in minimal displacement and trauma, with only a resultant minimum damage to the bone cells. This goal is best achieved with a body including a pattern of flute each of which presents a flattened tip edge.

Several reasons support this consideration. One reason is that the pattern of flutes increases the surface area of the body of the implant significantly when compared with an implant having a smooth body surface. It was indicated heretofore, that an increase of as much as 47%, or more, may be expected for an implant otherwise of like specifications. Another reason is that each flute of the pattern of flutes provides a tip that cuts through the bone within the anchor site. A further reason is that each flute of the pattern of flutes provides less trauma to the bone cells during pressed fitting than does the implant that is threaded into the anchor site.

Figure 6:
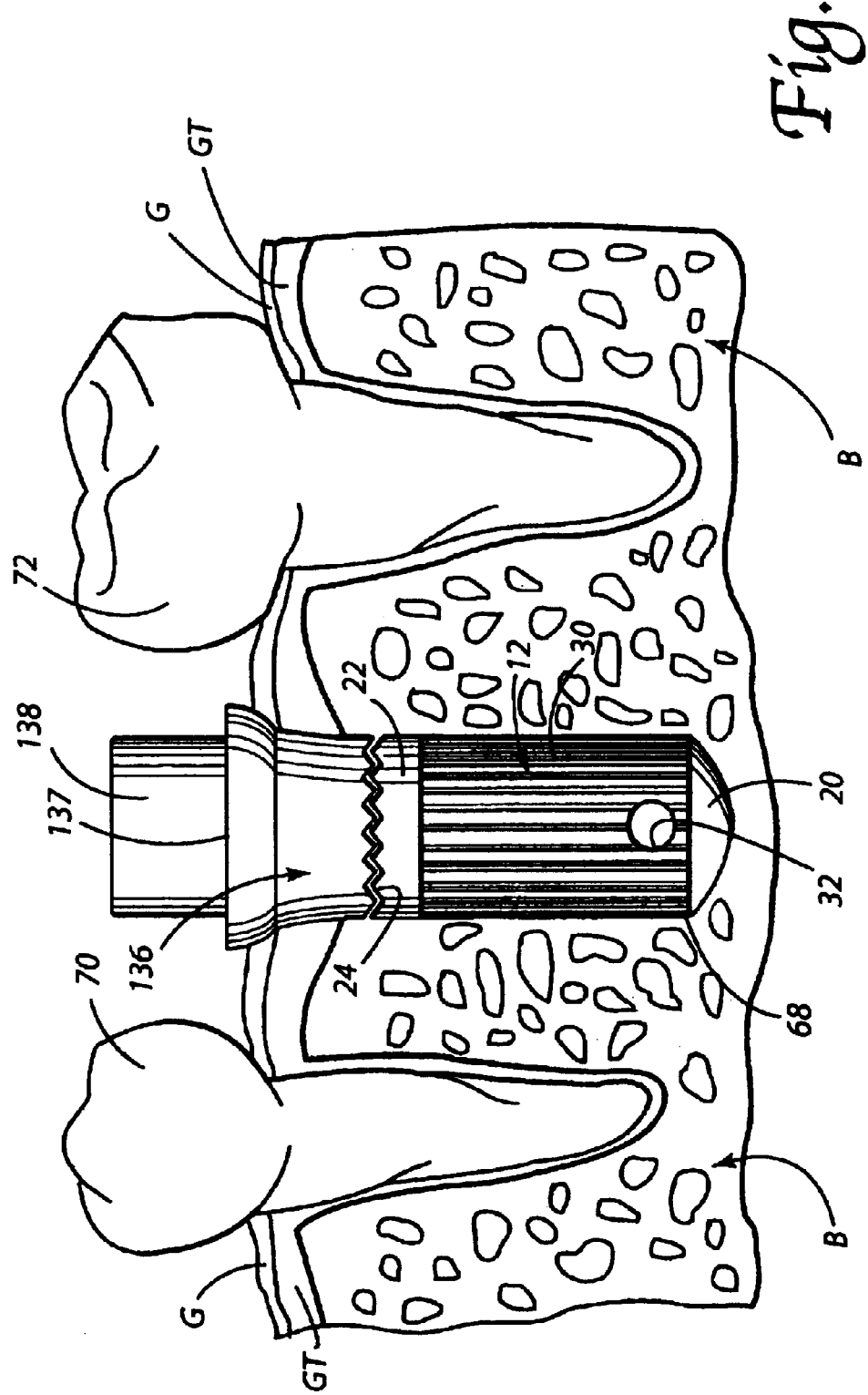
Figure 7:
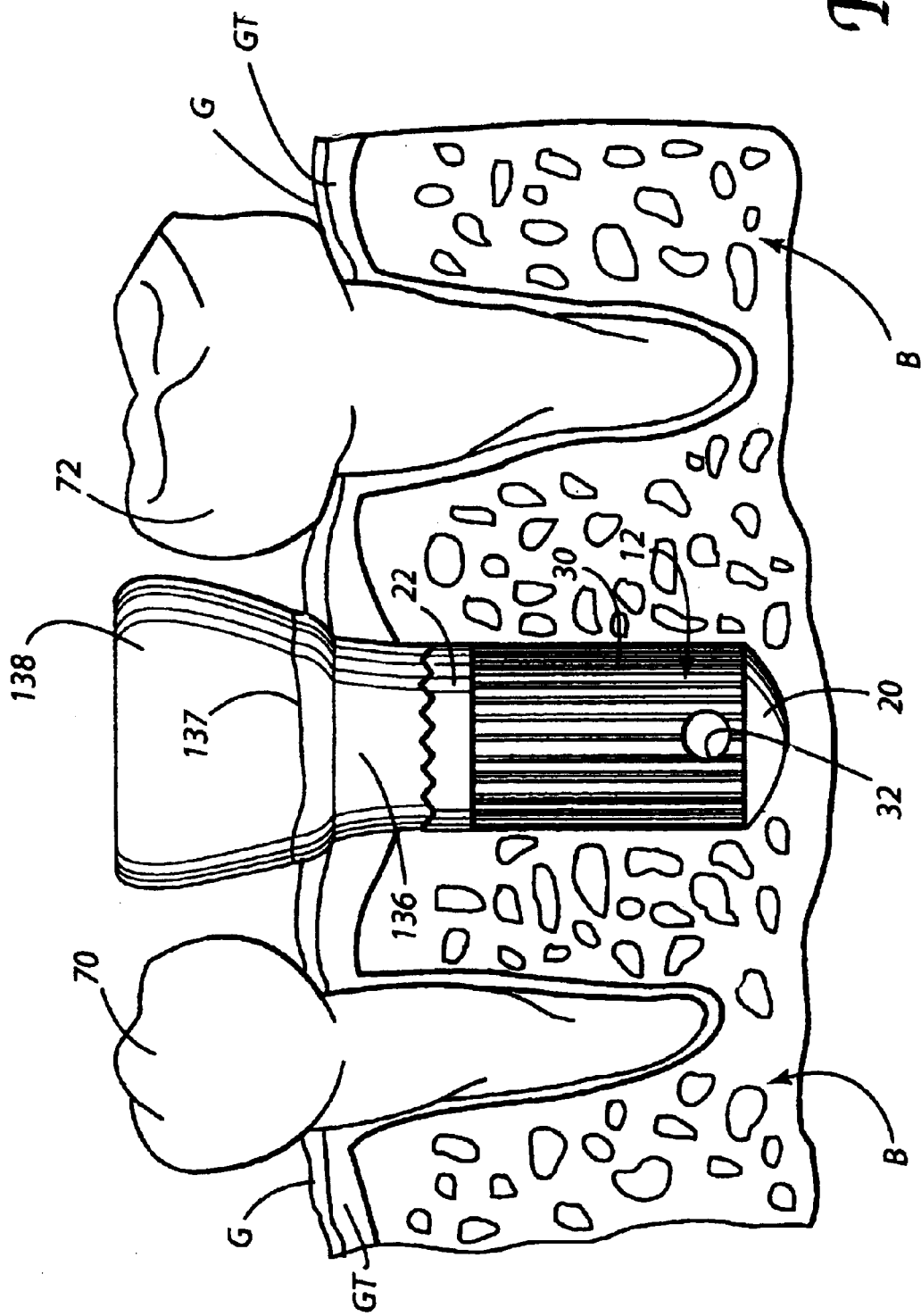
Figure 8:
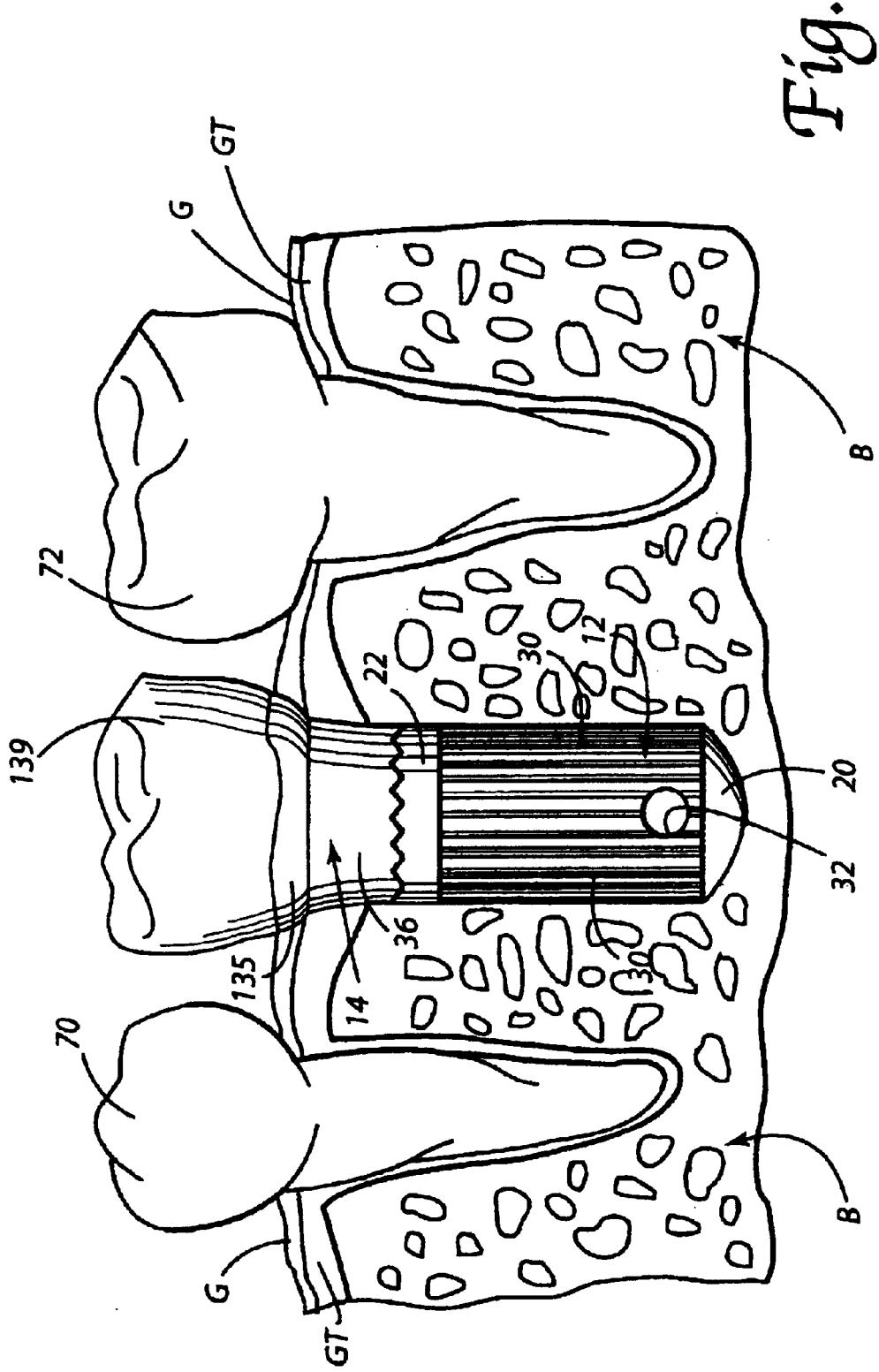

In FIGS. 6 through 8, implant 12 is illustrated in the fully seated position within anchor site 68, and a temporary abutment 136 is illustrated (see FIG. 6) in position poised over implant 12. The mounting surface of temporary abutment 136 is complementary to the surface outline of mounting surface 24 of implant 12. Both mounting surfaces are illustrated by a representative sawtooth pattern, and in positions of alignment (see FIG. 6). Fastener assembly 16 is used to connect both implant 12 and temporary abutment 136. Through action of the fastener assembly 16, as will be discussed, implant 12 and temporary abutment 136 are mounted together as the mounting surfaces are drawn to a juxtaposed surface-to-surface relationship. The complementary patterned structure on the mounting surfaces essentially lock both the implant and temporary abutment in the mounted position. The temporary abutment may be considered as a "healing abutment" placed by the dental surgeon and removed by the dentist or dental surgeon once the period of healing has run its course. The temporary abutment 136 when it is removed is replaced by the permanent abutment 12 including mounted prepable member 135.

Temporary abutment 136 preferably is formed of a material having strength in support of a temporary restoration 138, and a capability of being worked or contoured by the restoring dentist or dental surgeon. Regarding the latter, for example, it is advantageous to work the temporary abutment 136 within the region of its upper surface 137 of a shoulder portion from a planar surface of a surface having a contour that follows substantially the line of contour of gum G (see FIG. 7). In this manner, the temporary abutment 136 placed in the oral cavity is fully concealed within the gingival tissue GT, below the line of gum G.

Temporary restoration 138 is formed of the same material as the temporary abutment 136. It, too, may be worked to contour a lower surface in a complementary fashion to that of temporary abutment 136 so that both surfaces along the seam of the structures are in surface-to-surface relation. This action encourages creation of a soft tissue emergence profile. The fabricating material is Artglass, the material discussed previously in connection with the discussion directed to prepable member 135.

FIG. 7 illustrates temporary restoration 138 supported by temporary abutment 136. Temporary restoration 138 may be secured on abutment temporary 136 by application of a coating of an adhesive (not shown) but similar to the layer 140 applied to one or the other or both confronting surfaces along abutment 14 and prepable member 135, in FIG. 1. As illustrated, these surfaces include the outer surface of neck 38 and an upper surface along shoulder 36. The material may be Kevloc, also previously described.

Finally, referring to FIG. 8, a final restoration 139 also providing a final match with the natural teeth 20, 22 may be mounted on abutment 14 and preparable member 135. This action follows removal of both the temporary members including temporary abutment 136 and temporary restoration 138. The final 139 restoration preferably will be an analog of the temporary restoration 138 with the same contoured seam along the interface with prepable member 135.

Fastener assembly 16 is unique in its operation as a fastener in connecting implant 12 and abutment 14 when the abutment is located to the mounted position and mounting surfaces 24, 44 are in juxtaposed position. Fastener assembly 16 operates to secure components with both mechanical and frictional securing capability.

In operation, sleeve 48 is mounted on fastener member 46 in a relaxed, mounted position and restrained within channel 57 by shoulders 56, 60. The various dimensional characteristics of fastener member 46 and sleeve 48 necessary to achieve the mounted relationship were discussed heretofore.

The interactive components of the fastener assembly 16 are introduced to the assemblage of implant 12 and abutment 14. Particularly, fastener member 46 is positioned with its leading end 54 at the opening into bore 40 of abutment 14. As also discussed, the dimensions of body 52 and bore 40 are substantially equal in cross-section thereby to permit body 52 to pass through bore 40 in abutment 14, including the counterbored length 42. Further movement of the fastener member 46 positions the leading end 54 of the fastener member 46 for threaded engagement within the threaded bore 28 of implant 12. Movement may be imparted to fastener member 46 rotationally by an Allen wrench or similar tool acting within an opening 156 of hexagonal or other non-circular shape (see FIG. 18). As apparent, should head 50 have a non-circular cross-section, movement may be imparted to fastener member 46 rotationally by a wrench or some other tool acting against the head.

As fastener member 46 is drawn further and further into threaded engagement sleeve 48 is drawn further and further into bore 40 of abutment 14. Also, as previously discussed, bore 40 has a diametrical dimension that is slightly less than the dimension of the outer surface 64 of sleeve 48 when in the relaxed condition. As further movement of fastener member 46 ensues, an increased length of the outer surface 64 to and beyond its mid-region of maximum outward bow interacts within and along bore 40 resulting in greater and greater deformation of sleeve 48 from the relaxed condition. Deformation is accompanied by closure of slit 66 toward a position at which the confronting edges move to a position of contact, and displacement of the inner and outer surfaces 62, 64 from the relaxed position to a position at which the surfaces locate substantially to concentric planes. The dimensions of bore 40 and sleeve 48 are chosen so that the sleeve deforms substantially throughout channel 57 into maximum frictional contact at the base of the channel and throughout the region of annular surfaces of shoulders 56, 60. The outer surface 64 of sleeve 48 during deformation will extend by a small increment beyond the outer extent of the channel and into maximum frictional contact with the surface along the interior of bore 40 of abutment 14.

Thus, fastener assembly 16 functions to provide a mechanical connection between implant 12 and abutment 14. To this end, the interaction of the threads along body 52 of fastener member 46 and the threads within the bore 28 of implant 12 acts to draw head 50 of fastener member 46 into engagement with neck 38 of abutment 14. As such, movement of implant 12 and abutment 14 is restrained in the axial direction. The compressive forces acting along mounting surfaces 24, 44 together with a resultant interaction of the complementary surface irregularities within the mounting surfaces also serve to restrain movement by locking implant 12 and abutment 14 in a rotational direction.

The fastener assembly 16, also, provides a frictional connection between abutment 14 and fastener member 46. The frictional connection created by sleeve 48 acting between and against fastener member 46 and the bore 40 of abutment 14 restrains movement of the fastener member 46 in the rotational direction.

Sleeve 158 comprising a modification of sleeve 48 is illustrated in FIG. 19. Sleeve 158 may be used with the fastener member 46 of fastener assembly 16 in substitution for sleeve 48. Sleeve 158 includes an inner and outer surface 160, 162 together with and a slit 164 extending through the surfaces from one end to the other. The surfaces 160, 162 of sleeve 158 generally are disposed in concentric planes. Sleeve 158 has a thickness equal to the spacing of inner and outer surfaces 160, 162 forming a pair of confronting surface at the extremes of slit 164. A protuberance 166 is carried by the outer surface 162 within a mid-length location. The protuberance, or preferably a plurality of protuberances 166 located at equidistant spacing around sleeve 158 provide the function of the mid-length, outward bow in surfaces 62, 64 of sleeve 48. Thus, the protuberances act against the surface of bore 40 of abutment 14 to deform the sleeve from the relaxed condition. As sleeve 158 deforms, the confronting surfaces move together, closing the slit. Inner surface, thus, is drawn into frictional contact with the surface of channel 57 and along the surfaces of shoulders 56, 60. Outer surface 162 also locates in a position of frictional engagement within bore 40. The area of frictional engagement acts at least between the region of each protuberance 166 and the surface within bore 40 as the fastener member is drawn into implant 12. While sleeve 158 has been found to function satisfactorily, sleeve 48 is the preferred sleeve in use of fastener member 16.

Figure 9:
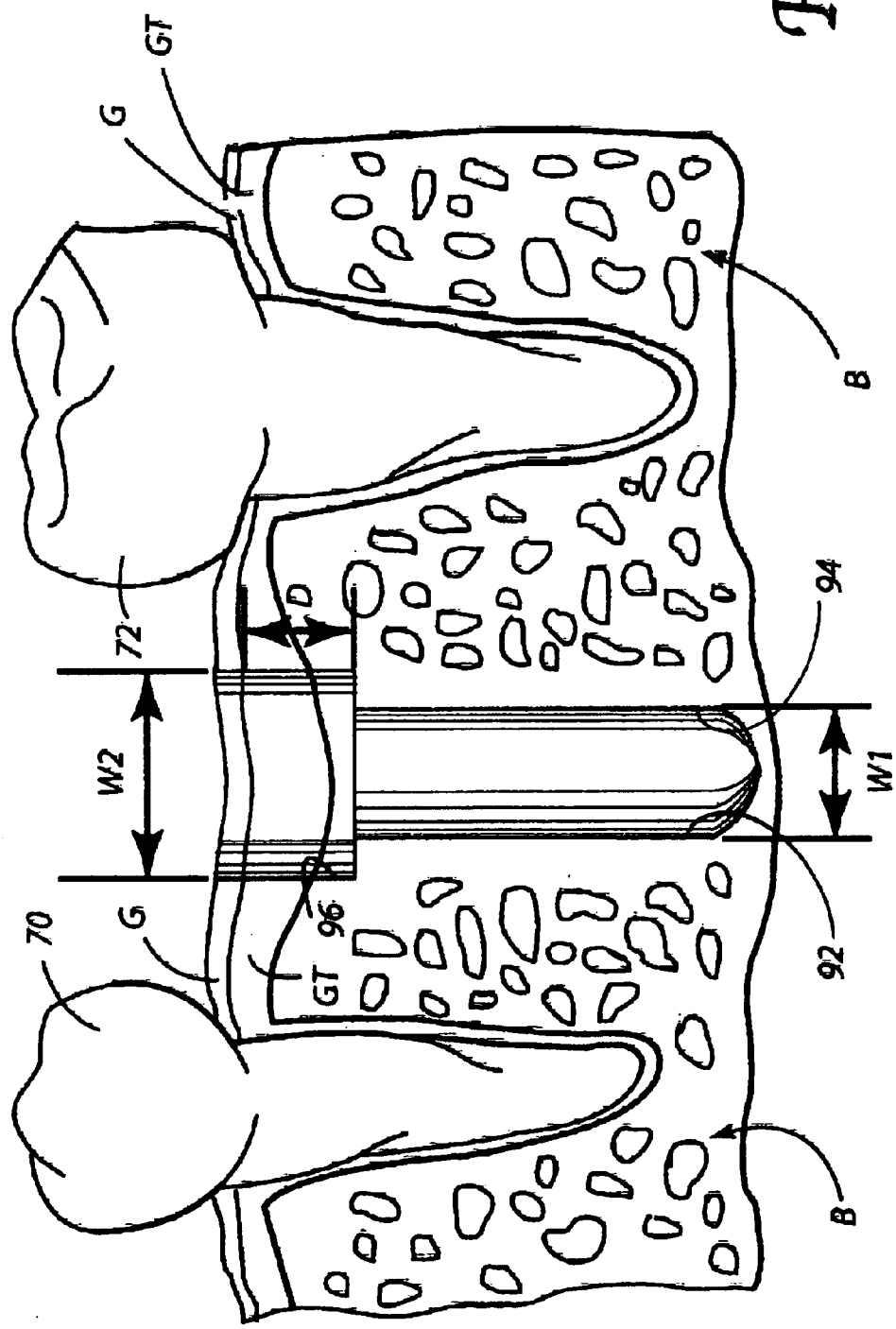
FIG. 9 is a schematic view similar to that of FIG. 3 illustrating a modified step in the dental restoration technique.

An anchor site 92 is illustrated in FIG. 9. This figure provides a view illustrative of a modification in a process step of the "two-step implantation technique." Anchor site 92 is formed by boring/drilling a first cut 94 of circular cross-section in jawbone B in the manner discussed in connection with the discussion directed to FIG. 3. The first cut 94 may be bored/drilled to any length. A second cut or countercut 96, also circular in cross-section, is bored/drilled into jawbone B, along the axis of first cut 94.

For purposes of the present discussion, first cut 94 may have a diametrical dimension W1 of 3 mm to 4 mm throughout its depth which may be cut to about 7 to 8 mm at a minimum and 15 mm at a maximum. Second cut 96 may have a diametrical dimension W2 of about 4 m to 6 mm and a depth D of about 3.5 mm. The second cut will accommodate both the shoulder and arch of a "large body" implant, such as an implant of the form of implants illustrated in FIGS. 10 through 13. The remaining depth of first cut 94 is sufficient to accommodate the implant when the body is in the fully seated position. As previously discussed, the neck of the implant when the body is in the fully seated position will extend only to a location within the layer of gingival tissue GT.

Figures 10, 11:
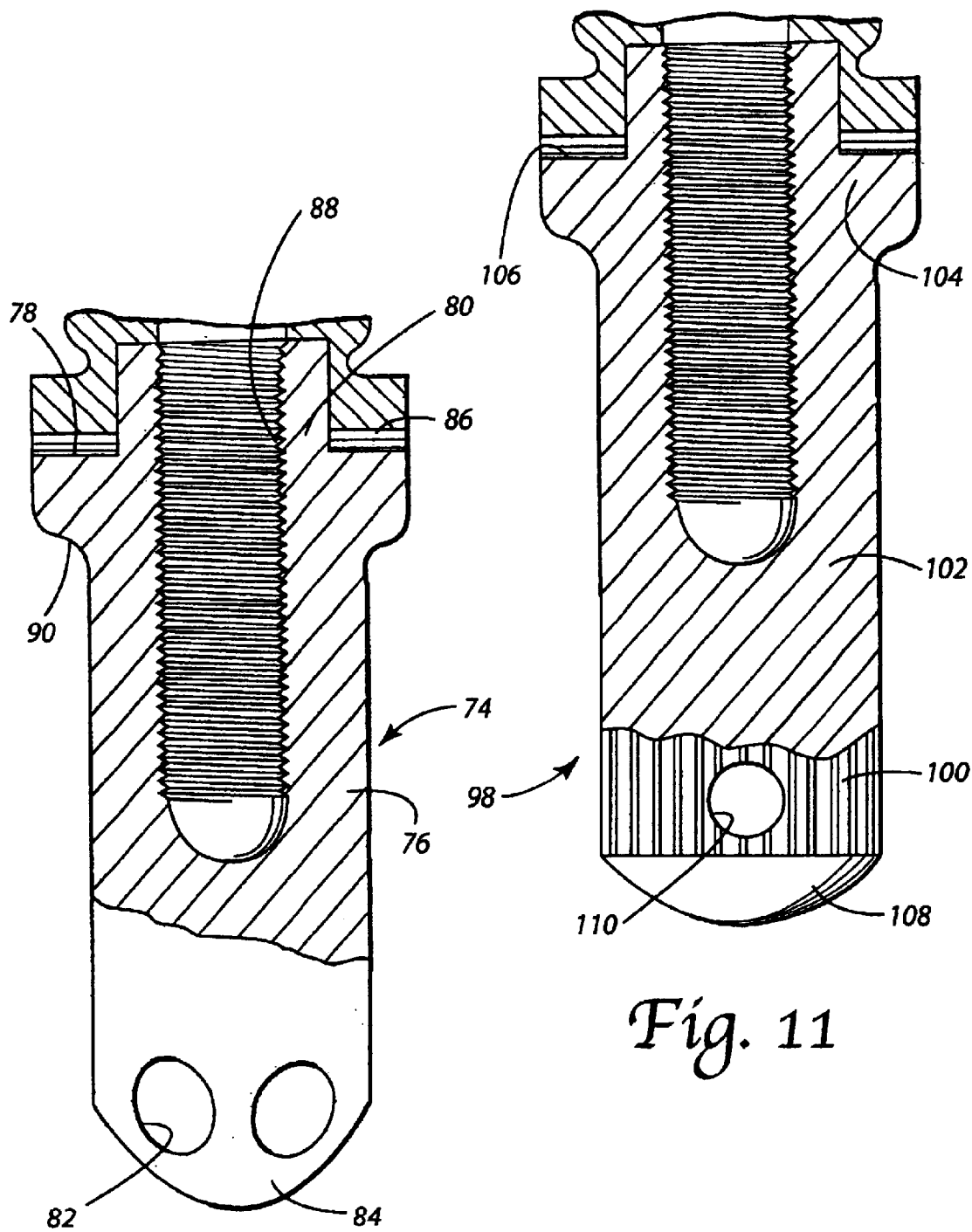
FIGS. 10 through 13 are views in elevation and partially in vertical section of several forms of implant of the dental restoration apparatus.
Figures 12, 13:
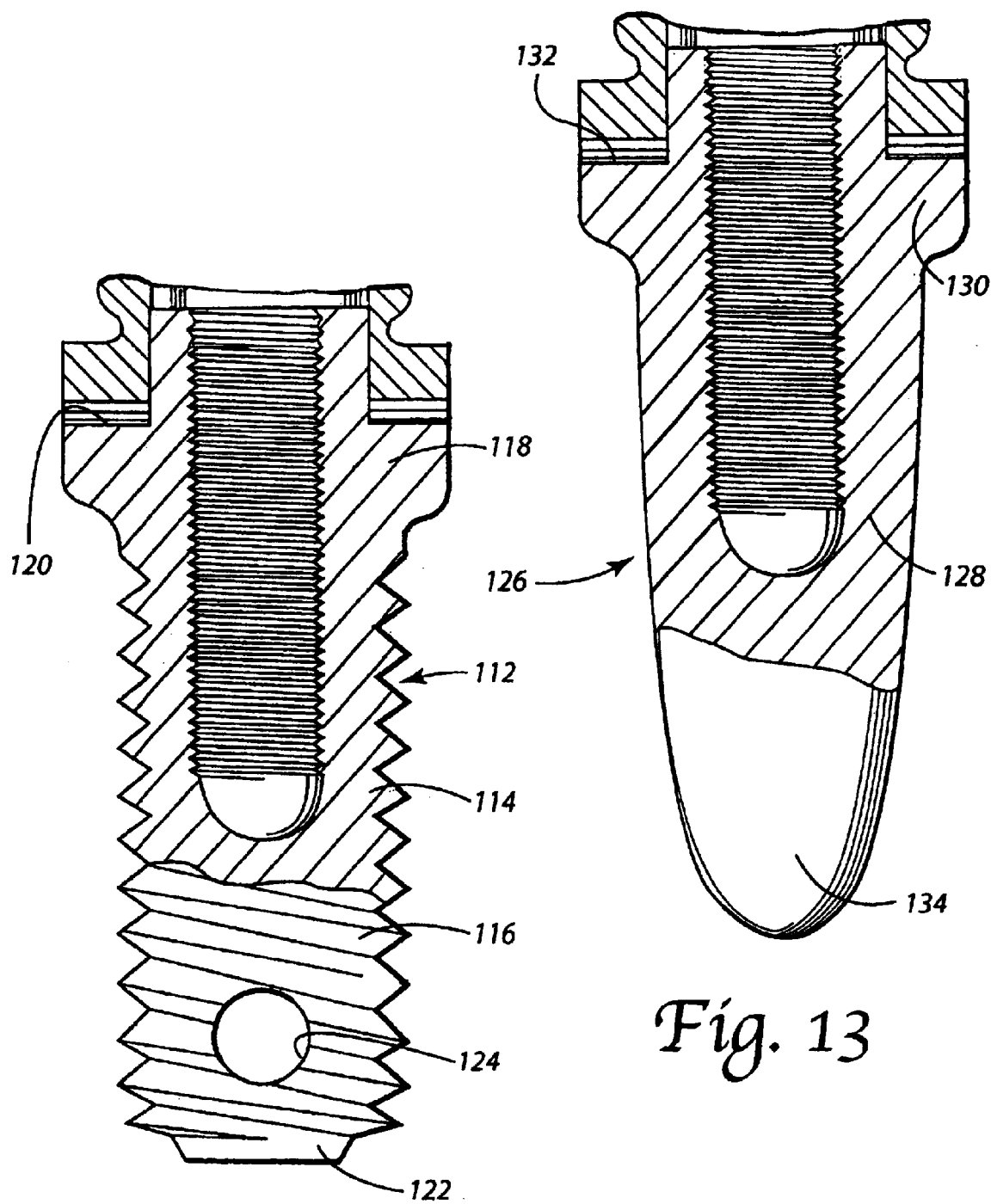

Referring to FIG. 10, implant 74 includes a body 76, shoulder 78 and a neck 80. Implant 74 is illustrative of one form of the so-called "large body" implant. Three (3) additional forms of implant will be discussed as the discussion of FIGS. 11 through 13 commence. With continued reference to FIG. 10, however, implant 74 includes a body 76 generally of a smooth surface construction throughout. Two openings 82 are illustrated at a leading end 84. Each opening may take the form either of an impression in the surface of body 76 or an entry to a passage extending within the body similar to the opening in implant 12 of FIGS. 1 and 2. In addition, the openings 82 may be representative of additional openings each arranged circumferentially about the body.

Neck 80 extends from body 76 from the region of shoulder 78. A mounting surface 86 extends beyond the region of neck 80 to the occlusal margin. And, a bore 88 extends through neck 80 along the axis of body 76. The bore 88 is threaded along its length.

The structures of implant 74 that are like or duplicative of structures heretofore described with regards to the discussion of implant 12, are not specifically described but should be considered to function generally in the same manner and for the same. This is also the case with the other of the so-called "large body" implants illustrated in FIGS. 11 through 13, discussed below.

Body 76 of implant 74 may have a diametrical dimension of about 3 to about 4 mm. Shoulder 78 has a larger diametrical dimension. For example, body 76 may have a diametrical dimension of 3 mm, and the shoulder 78 may have a diametrical dimension of 4 mm. In another example, body 76 may have a diametrical dimension of 4 mm, and shoulder 78 may have a diametrical dimension measured at the occlusal margin of about 5 mm to about 6 mm. Thus, shoulder 78 serves the purpose of providing a mounting surface 86 between implant 74 and abutment 14 that is larger than the body in diametrical dimension and site specific for a replacement tooth located in different areas of jawbone B within the oral cavity. For example, shoulder 78 may provide a mounting surface 86 and interface with mounting surface 44 of abutment 14 of 6 mm within the molar area, of 5 mm within the bicuspid area, and of 4 mm within the incisor area. Body 76 of implant 74 used in the incisor area typically will be about 3 to about 3.5 mm in diametrical dimension.

With continued reference to FIG. 10, an arch 90 connects shoulder 78 and body 76 of implant 74. Arch 90 may extend along an angle of curvature of about 80° according to American Standard Machine Screw Angle specifications. As such, arch 90 provides a gentle curve blending shoulder 78 into body 76. Arch 90 may extend through a vertical height of about 1.5 mm, while the height of the shoulder measured from the occlusal margin to the arch may be about 2.0 mm.

It is believed that the arch design better distributes the resultant forces both from vertical loading and loading through lateral extraneous forces to the surrounding bone. It is also believed, from a mechanical engineering standpoint, that the distribution of forces is substantially equal along each increment of length of curvature of arch 90. Thus, vertical and/or lateral loading on the implant may be managed in better fashion, to better preserve the viable bone. The manner of distribution of forces equally along the arch provides the viable bone tissue within which the implant resides. And, because of its "living" nature the viable bone tissue has an opportunity to repair itself. Therefore, if the tissue is properly treated the chance of breakdown may be reduced. If viable tissue breaks down for whatever reason, including a response to unfavorable loading forces, bone is lost and replaced with fibrous tissue. The result may be the creation of periodontal pockets resulting in additional bone disease and implant loss. These pockets and resultant cervical bone loss around the margin of the body of the implant, and loading table, occurs following placement of many implants. Unfavorable loading forces directed from both the vertical and lateral directions also results in cervical bone loss. The bone loss has a distinct tendency to migrate apically. The implant, then, begins to lose the ability to function as a base or anchor for the restorative structure. The loss in stability evidenced by vibration or a shimmy effect only compounds the problem of bone loss adjacent the implant and abutment.

Implant 98 (see FIG. 11) is substantially identical in construction to that of implant 74, in that implant 98 includes a shoulder 104 within the region of the trailing end. Implant 98, however, differs from implant 74 in that body 102 supports a family of flutes comprised of one or more individual flutes 100. The family of flutes is formed on body 102, and each flute of the family extends along the outer surface of the body in an attitude that is substantially parallel with the axis. The flutes of the family of flutes extend from a location below shoulder 104 to a location within the region of leading end 108. In this respect, implant 98 duplicates the construction of implant 12 discussed with specificity, above.

Implant 98, also like implant 12, includes one or more openings 110 within leading end 108. Flutes 100 comprising a family of flutes and the openings may function in concert to increase the surface area of body 102 of implant 98 exposed to adjacent bone tissue and enhance the capability of adherence and attachment of bone tissue to body 102 during the healing process. This has been discussed in detail. Implant 98 likewise is pressed fit into anchor site 92.

Body 114 of implant 112 (see FIG. 12) likewise includes a shoulder 118 and mounting surface 120. As such, implant 112 duplicates substantially the construction of implant 74. Implant 112, however, differs from implant 74 in that body 114 carries a threaded pattern 116 along the outer surface from a location below shoulder 118 to a location at or within leading end 122. Thus, implant 112, however, is threaded rather than pressed fit into anchor site 92. To this end, implant 112 may be placed in tapped bone or moved to the seated position as the threads self-tap a path. The threaded pattern 116, as discussed in connection with the discussion directed to other forms of implant, increases the area of surface exposed to adjacent bone tissue. It is also believed that the threaded implant 112 gains immediate increased stability in the anchor site when compared to pressed-fit, frictionally-stable implants. The opening or openings 124 within the region of leading end 122 of the character as also discussion function to increase the surface area of implant juxtaposed to bone tissue within the anchor site to assist in the integration of implant to bone during osseointegration.

Implant 126 (see FIG. 13) somewhat duplicates implant 74 in construction. To this end, body 128 of implant 126 is of smooth surface construction throughout. Body 128, however, is tapered in outline from the region of shoulder 130 and mounting surface 132 to leading end 134. Implant 126 is also pressed fit into anchor site 92. Implant 126 because of the tapered outline toward leading end 134 may be used with great benefit at locations within the oral cavity where the amount of bone within which an anchor site is created is limited.

A dental restoration apparatus 10 including an implant like implants 12 and 98 have been used, and used with success, in combination with abutment 14 and fastener assembly 16. A construction of implant typified by implant 12, however, is preferred in use in the dental restoration apparatus. Implants having a shoulder have been used successfully. To this end, these implants have been found to react well to the forces of mastication focused both in the vertical and lateral directions at a mounting surface at the interface of an implant/abutment/dental restoration. The arch design, it is believed, functions to better distribute the resultant forces both from vertical loading and loading through lateral extraneous forces satisfactorily to the surrounding bone. It is also considered that the two (2) forms of implant preserve the viable bone between adjacent implants and between an implant and an adjacent natural tooth or teeth in larger quantities. Finally, the implants have a significantly larger surface area exposed to the viable bone tissue within an anchor site, to integrate better with the tissue and enhance the process of osseointegration. The larger surface area is created by fabricating the body of the implant with a pattern of flutes extending from the region of the trailing end of the body to the region of the leading end. As discussed, an increase of about 50% may be realized.

An implant also may be mounted within the jawbone B of the patient following a so-called "one-stage implantation technique." This technique follows generally the steps of the two-stage technique, yet utilizes an implant structure in a process technique that differs slightly in technique from the technique discussed previously. The main difference is in one aspect of the overall technique is in the use of an implant while it is similar either to implant 12, or implant 98, that includes a neck that is longer in length (see FIG. 14). According to the one-stage technique, the neck is non-submerged when the implant is seated.

Figure 14:
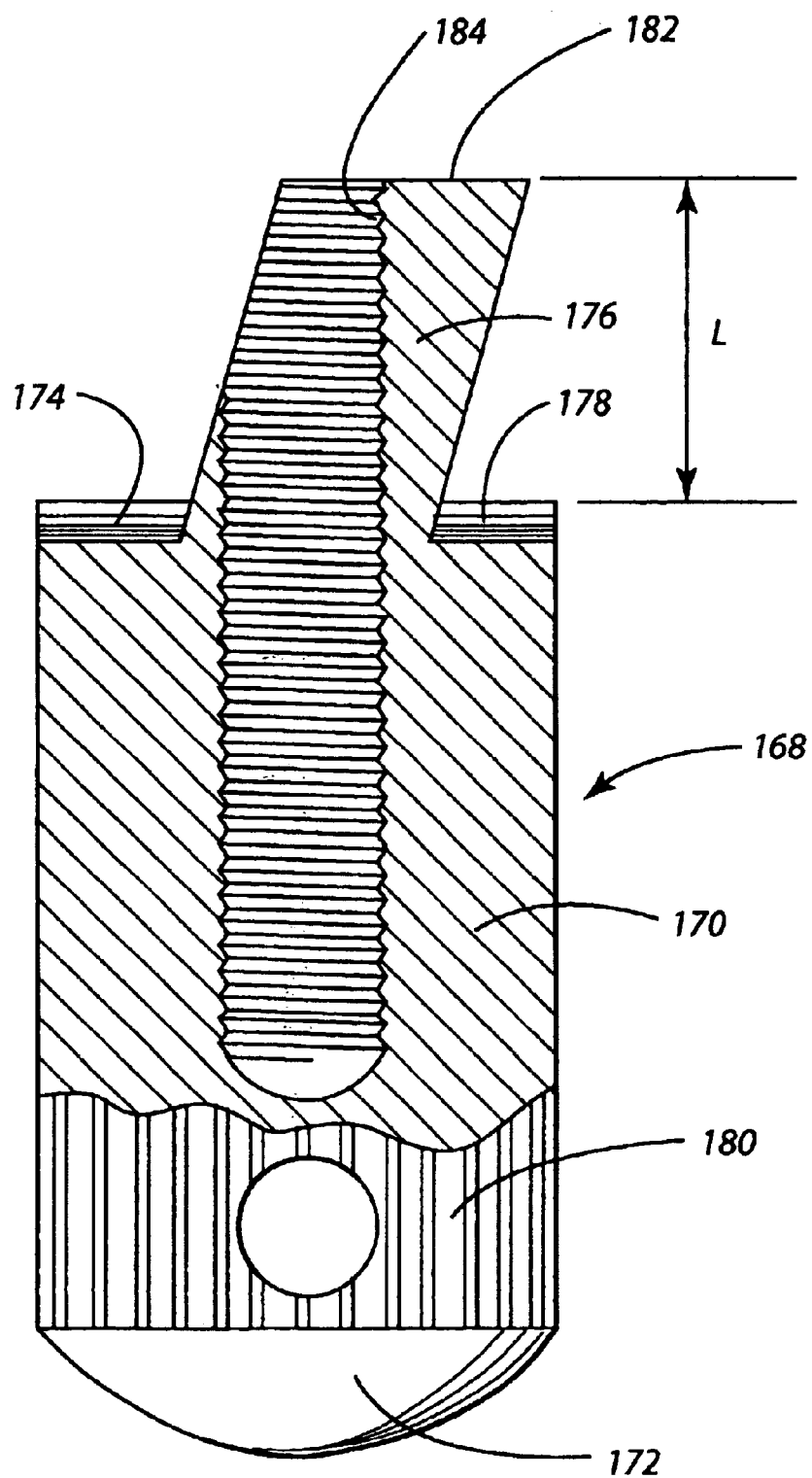
FIG. 14 is a view in elevation and partially in vertical section of an implant like the implant of FIG. 1, but modified in construction at the trailing end.

FIG. 14 illustrates implant 168 including a body 170 having a leading end 172 and a trailing end 174. A neck 176 extends from the trailing end 174 and mounting surface 178. In addition, the body provides a pattern of flutes 180 extending along the body within the region of the leading and trailing ends 172, 174. Implant 168, as described, duplicates the structure of implant 12, and generally duplicates the structure of implant 98. It should be apparent, however, that implant 168 within the teaching of the invention could be fabricated with a shoulder like the shoulder on any one of the forms of implant illustrated in FIGS. 10 through 13. As such, implant 168 would also duplicate the structure of implant 98.

Implant 168 differs with regard to implants previously discussed in connection with the feature of length of neck 176 extending from trailing end 174, and in certain circumstances with the feature of the specific attitude of direction the neck may take. It was indicated that neck 176 of implant 168 is longer than the neck of an implant used in the one-stage technique. Actually, neck 176 may be of a length to extend a distance L of about 5 mm from the trailing end 174 and mounting surface 178. As such, neck 176 in the non-submerged orientation will extend beyond anchor site 68, 92 and through both the gingival tissue GT and gum G when implant 168 is positioned in the seated position. This feature is in contrast to the implant and disposition of the neck in the two-stage process.

An important advantage is derived through use of the one-stage technique. The advantage resides in the fact that the neck 176 of implant 168 is non-submerged. Thus, there is no need for a secondary cut within the gingival tissue GT to remove temporary components, such as the temporary abutment 136 and temporary restoration 138 prior to mounting an abutment and prepable member 135. It is likely that excellent soft tissue healing will occur around the emergence profile portion of the implant. The one-stage process also facilitates monitoring of work during the healing phase as the process of osseointegration runs its course. If the process of osseointegration is not progressing successfully, it is possible to undertake necessary and proper remedial actions. The one-stage process also increases the dentist's or dental surgeon's efficiency because soft tissue healing is completed during the healing phase. It is also much easier to obtain impressions and a good record of soft tissue implant anatomy.

The one-stage technique envisages use of a prepable abutment to replace a temporary abutment after the integration period, and a permanent restoration capable of mounting on the prepable abutment. The manner of mounting the permanent restoration and the manner of mounting both abutments to the implant, as well as both restorations to one or the other or both abutments follows the discussion directed to the two-stage technique.

Referring, again, to FIG. 14 it is seen that neck 176 is at an angle relative to the axis of body 170. The illustration represents neck 176 in one of several attitudes that neck 176 may take within a range of from 0° to about 15°. Positioning of the abutment received on neck 176, as previously discussed, may be important to accommodate bone anatomy and occlusal needs.

Neck 176 preferably is circular in cross-section throughout its length. The outline of neck 176 at end 182, however, is either circular or somewhat oval outline depending upon whether neck 176 extends coaxially of body 170 or at some angle relative to the axis. Neck 176 may be pressed fit into a seated position within anchor site 68, 92. A bore 184 is formed in body 170, through neck 176. Bore 184 is threaded for purposes previously discussed.

I claim:

1. A fastener assembly for mounting together components of a dental restoration comprising
    a fastener member having
        a head and
        an elongated body formed about an axis through said head extending to a distal end having
            a first portion of diameter D extending from said distal end toward said head, said first portion being threaded externally from said end throughout at least part of its overall length,
            a second portion of cylindrical outline of diameter D1 (wherein D1<D) extending from said first portion toward head, and
            a shoulder at the juncture of said first and second portions, and
    a sleeve member formed of resilient material mounted on said elongated body within and along said second portion, said sleeve member having
        an inner surface,
        an outer surface,
        an axial length in relaxed condition substantially equal to the length of said second portion,
        a slit through both said surfaces from end-to-end creating opposed, spaced-apart, confronting surfaces throughout said length, and
        opposite end surfaces each defining a substantially continuous ring having an inner diameter S1 (wherein S1>D1 and<D) and an outer diameter S(wherein S>D) so that at least a portion of an end surface of said sleeve member in mounted location is retained against said shoulder, and
    means providing a surface for retaining at least a portion of the opposite end surface of said sleeve member, said retaining means spaced from said shoulder defining the length of said second portion.

2. The fastener assembly of claim 1 wherein said retaining means is coextensive with the undersurface of said head.

3. The fastener assembly of claim 1 wherein said retaining means includes a surface in part inclined outwardly and in part coextensive with the undersurface of said head.

4. The fastener assembly of claim 1 wherein said inner and outer surfaces of said sleeve member between opposite end surfaces are bowed outwardly to substantially a mid-point location.

5. The fastener assembly of claim 1 wherein said inner and outer surfaces of said sleeve member are disposed substantially within concentric planes along diameters S1 and S, respectively.

6. The fastener assembly of claim 5 comprising at least one protuberance, each said protuberance formed on said outer surface of said sleeve member substantially at a mid-point location between opposite end surfaces.

7. The fastener assembly of claim 6 comprising a plurality of protuberances, each protuberance located substantially equidistantly from adjacent protuberances on said outer surface.

8. A fastener for engaging and positively resisting loosening from a workpiece comprising
    an elongated body including
        a head at one end,
        a threaded portion extending toward said head from the other end, said elongated body at least along the length of said threaded portion having a first diametrical dimension, and
        a channel of a second, smaller diametrical dimension formed in said body between said head and threaded portion,
    a sleeve member formed of resilient material received in said channel circumferentially about said elongated body, said sleeve member having
        an inner surface,
        an outer surface having a second diametrical dimension greater than said first diametrical dimension, and
        a slit through both said surfaces from end-to-end of said sleeve member creating opposed, spaced-apart, confronting surfaces, and
    means on said sleeve member responsive to a compressive action exerted by said workpiece for moving said confronting surfaces toward one another closing said slit and reducing said second diametrical dimension as well as the diametrical dimension of said inner surface so that said inner surface substantially along the length of said sleeve member frictionally engages said elongated body thereby binding said fastener against loosening.

9. The fastener of claim 8 wherein each said responsive means comprises an outwardly bowed, substantially mid-point location around said outer surface which yields as a result of forces exerted by said workpiece on said outer surface during initial and final tightening.

10. The fastener of claim 8 wherein said responsive means comprises at least one protuberance generally within a mid-point location of said outer surface which yields as a result of forces exerted by said workpiece on said outer surface during initial and final tightening.

11. The fastener of claim 10 wherein said responsive means includes a plurality of protuberances, each protuberance located at substantially equidistant spacing, one from another.

12. The fastener of claim 8 wherein said elongated body further includes a channel portion having a third diametrical dimension less than said first diametrical dimension, said channel portion located between said threaded portion and head, a shoulder at the juncture of said threaded portion and channel portion, said sleeve member received circumferentially around said channel portion in position that one end of said sleeve member is limited in movement axially against said shoulder, and means providing a surface for restraining movement of the other end of said sleeve member.

13. The fastener of claim 12 wherein said sleeve member has a length substantially equal to the length of said channel portion.

14. The fastener of claim 12 wherein said restraining surface comprises an undersurface of said head around said elongated body.

15. The fastener of claim 12 wherein said restraining surface in part is inclined outwardly and in part coextensive with the undersurface of said head.

16. A fastener assembly for insertion through a bore of a first workpiece into a threaded bore of a second, axially aligned workpiece to engage said workpieces and positively resist relative rotational movement of said first workpiece and fastener assembly, said fastener assembly comprising
a fastener member including
an elongated body substantially of cylindrical cross section throughout, said elongated body having
a head located at one end,
a first portion of diameter D having a threaded length extending from the other end,
a second portion between said head and said first portion having a diameter D1 (wherein D1<D), and
a shoulder at the juncture of said first and second portions,
a sleeve member formed of a resilient material mounted on said elongated body within and along said second portion, said sleeve member including
inner and outer surfaces,
a length in relaxed condition substantially equal to the length of said second portion,
a slit between said surfaces extending the length of said sleeve member providing opposed, confronting sleeve member surfaces, and
opposite end surfaces each defining a substantially continuous ring having an inner diameter S1 (wherein S1>D1 and<D) and an outer diameter S(wherein S>D) so that at least a portion of an end surface is retained against said first shoulder when said sleeve is mounted, and
means providing a surface for retaining at least a portion of the opposite end surface of said sleeve member, said retaining means spaced from said shoulder defining the length of said second portion,
whereby entry of said fastener assembly into said bore of said first workpiece, movement axially from said position of entry to a position that said threaded length of said first portion begins to engage in said threaded bore of said second workpiece and said sleeve member distorts from said relaxed condition to a final condition when said threaded length engages fully within said threaded bore represented by movement of said confronting sleeve surfaces toward one another to close said slit substantially completely, and compress said sleeve member to an outer surface diameter S2 (wherein S2>D) so that said inner surface engages frictionally said elongated body and said outer surface engages frictionally said surface of the bore of said first workpiece to positively resist relative rotational movement and loosening of said fastener assembly and workpieces.

17. The fastener assembly of claim 16 wherein said inner and outer surfaces of said sleeve member are bowed outwardly to substantially a mid-point between opposite end surfaces.

18. The fastener assembly of claim 16 wherein said inner and outer surfaces of said sleeve member are located substantially in concentric cylindrical planes along diameters S1 and S, respectively.

19. The fastener assembly of claim 18 comprising at least one protuberance, each protuberance formed on said outer surface of said sleeve member substantially at a mid-point between opposite end surfaces.

20. The fastener assembly of claim 19 comprising a plurality of protuberances located equidistantly from adjacent protuberances around said outer surface.

21. The fastener assembly of claim 16 wherein said shoulder and retaining means are disposed within planes perpendicular to an axis through said elongated body.

22. The fastener assembly of claim 21 wherein the outer diameter of said shoulder is less than the outer diameter of said sleeve member when mounted on said elongated body within and along said second portion.

23. The fastener assembly of claim 16 wherein said first and second workpieces comprise an abutment member and an implant member, respectively, of a dental restoration.

24. The fastener assembly of claim 16 wherein said head engages a surface surrounding said bore of said first workpiece following full threaded engagement of said first portion of said elongated body and in said threaded bore of said second workpiece.

25. The fastener assembly of claim 16 wherein said second portion of said elongated body resides completely within said first workpiece when said workpieces are assembled.

26. Dental restoration apparatus comprising
an implant member adapted for implantation within the jaw bone of a patient having
an implant body formed about a first axis including
a leading end,
a trailing end providing a first mounting surface, and
a bore extending from said trailing end into said body along an axis coaxial with said first axis, said bore being threaded substantially along its length,
an abutment member having
an abutment body formed about a second axis including
a leading end providing a second mounting surface,
a trailing end, and
a bore whose axis is coaxial along a second axis extending throughout said body,
said abutment member adapted to be mounted on said implant member in position that said first and second axes are coaxial and said first and second mounting surfaces contact one another, and
a fastener assembly including
a fastener member providing
a head and
a body formed about a third axis extending through said head to an end including
a first portion of a first diameter substantially along its length
a second portion of a second, larger diameter extending from said end toward said first portion threaded substantially throughout its length, and
a shoulder separating said first and second portions, and
a sleeve member of resilient material supported by said body within said first portion including
inner and outer surfaces,
a slit between said surfaces extending from one end to the opposite end of said body providing opposed, confronting surfaces of said sleeve member, an axial length in a relaxed condition substantially equal to the length of said first portion, and said opposite ends of said body defining ring surfaces whose inner diameter is less than said second diameter for support of a ring surface against said shoulder, whereby said fastener member once moved through said abutment member for full threaded receipt in said implant bore secures said implant and abutment members between said head and threaded length of said second portion tightly along confronting first and second mounting surfaces, and said sleeve member through action of said bore of said abutment member closes from said relaxed position to secure said abutment member rotationally by frictional gripping action between said sleeve member, abutment bore and fastener member.

27. The dental restoration of claim 26 wherein both said first and second mounting surfaces are located in planes substantially perpendicular to said first and second axes, respectively.

28. The dental restoration of claim 26 wherein said first mounting surface includes at least one surface irregularity, and said second mounting surface also includes at least one complementary surface irregularity, whereby said abutment and implant bodies may be mounted together in at least one fixed, angular position.

29. The dental restoration of claim 28 including a pattern of surface irregularities in said first mounting surface, a complementary pattern of surface irregularities in said second mounting surface, and each surface irregularity in each mounting surface located at substantially an equiangularly spaced location from an adjacent irregularity, whereby said abutment and implant bodies may be mounted together in a plurality of fixed, angular positions.

30. The dental restoration of claim 26 wherein said implant body further includes an outer surface between said leading and trailing ends within the region of an outer periphery of said first mounting surface.

31. The dental restoration of claim 30 wherein said outer surface is substantially cylindrical.

32. The dental restoration of claim 30 wherein said outer surface is tapered toward said leading end.

33. The dental restoration of claim 30 wherein said implant body further includes at least one ridge formed on said outer surface extending substantially the distance between said leading end and an outer peripheral portion of said first mounting surface.

34. The dental restoration of claim 33 wherein each ridge includes
  a first surface substantially of arcuate outline,
  a second surface of similar outline, and
  a surface connecting said first and second surfaces.

35. The dental restoration of claim 34 wherein said connecting surface is angled substantially toward an outer terminating edge.

36. The dental restoration of claim 34 wherein said connecting surface is substantially flat.

37. The dental restoration of claim 33 including a plurality of ridges formed on said outer surface, each said ridge spaced apart substantially equidistantly from an adjacent ridge.

38. The dental restoration of claim 30 wherein said outer peripheral region of said first mounting surface extends into a shoulder of a dimension larger than that of said body, and an undersurface connecting an outer peripheral region of said shoulder with said outer surface, said undersurface including a length that is outwardly arcuate.

39. The dental restoration of claim 26 wherein said implant body further includes a post extending from said first mounting surface.

40. The dental restoration of claim 39 wherein said post is cylindrical in outline.

41. The dental restoration of claim 39 wherein said post is irregular in outline.

42. The dental restoration of claim 39 wherein said post includes a threaded bore throughout its length coaxial with said first axis.

43. The dental restoration of claim 39 wherein said post extends along a fourth axis forming an angle $\Theta$ at the intersection of said first axis, and including a threaded bore coaxial with said first axis.

44. The dental restoration of claim 43 wherein said angle $\Theta$ is encompasses about 0 to about 15°.

45. The dental restoration of claim 43 wherein said angle $\Theta$ is about 15°.

46. The dental restoration of claim 26 wherein said abutment body includes a neck, said neck extending from said trailing end of said body along said second axis defining an annular shoulder at the base of said neck, said shoulder providing a third mounting surface adapted for supporting a restoration.

47. The dental restoration of claim 38 wherein said bore throughout said abutment body is counterbored from said mounting surface of said leadling end, said counterbore adapted to receive said neck of said implant body when said implant and abutment bodies are mounted together.

48. The dental restoration of claim 46 wherein at least said third mounting surface of said abutment body is formed of a prepable material adapted to be contoured to match the contour of the gum line of the dental patient.

49. The dental restoration of claim 26 wherein said implant body of said dental restoration includes at least a titanium metal surface coating.

* * * * *